United States Patent
Lind et al.

(10) Patent No.: US 11,686,726 B2
(45) Date of Patent: Jun. 27, 2023

(54) METHOD AND SYSTEM FOR SEPARATING BIOMOLECULES

(71) Applicant: GE Healthcare Bio-Sciences AB, Uppsala (SE)

(72) Inventors: Ola Lind, Uppsala (SE); Johan Fredrik Avallin, Uppsala (SE); Andreas Torbjorn Lundin, Uppsala (SE); Nils Norrman, Uppsala (SE); Ronnie Palmgren, Uppsala (SE); Gustav Jose Rodrigo, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 273 days.

(21) Appl. No.: 16/470,607

(22) PCT Filed: Dec. 27, 2017

(86) PCT No.: PCT/EP2017/084620
§ 371 (c)(1),
(2) Date: Jun. 18, 2019

(87) PCT Pub. No.: WO2018/122246
PCT Pub. Date: Jul. 5, 2018

(65) Prior Publication Data
US 2020/0087614 A1  Mar. 19, 2020

(30) Foreign Application Priority Data

Dec. 28, 2016 (GB) ..................................... 1622304
Dec. 28, 2016 (GB) ..................................... 1622305
Dec. 28, 2016 (GB) ..................................... 1622307

(51) Int. Cl.
| | |
|---|---|
| *G01N 33/543* | (2006.01) |
| *C12M 3/00* | (2006.01) |
| *C12M 3/06* | (2006.01) |
| *C12M 1/00* | (2006.01) |
| *C12M 1/34* | (2006.01) |
| *C12N 13/00* | (2006.01) |
| *B01D 21/00* | (2006.01) |
| *B03C 5/00* | (2006.01) |
| *B03C 5/02* | (2006.01) |
| *B03C 1/30* | (2006.01) |
| *B03C 1/28* | (2006.01) |
| *B03C 1/01* | (2006.01) |

(52) U.S. Cl.
CPC ... *G01N 33/54326* (2013.01); *B01D 21/0009* (2013.01); *B03C 1/30* (2013.01); *B03C 5/00* (2013.01); *B03C 5/02* (2013.01); *C12M 23/48* (2013.01); *C12M 27/16* (2013.01); *C12M 29/00* (2013.01); *C12M 41/44* (2013.01); *C12M 45/07* (2013.01); *C12M 47/04* (2013.01); *C12M 47/10* (2013.01); *C12N 13/00* (2013.01); *G01N 33/5436* (2013.01); *B03C 1/01* (2013.01); *B03C 1/288* (2013.01); *B03C 2201/26* (2013.01); *G01N 2333/31* (2013.01)

(58) Field of Classification Search
None
See application file for complete search history.

(56) References Cited

U.S. PATENT DOCUMENTS

| | | | |
|---|---|---|---|
| 6,471,860 B1 * | 10/2002 | Miltenyi | B03C 1/288 |
| | | | 210/695 |
| 2005/0019755 A1 | 1/2005 | Marchessault et al. | |
| 2013/0143313 A1 | 6/2013 | Niazi | |
| 2013/0244322 A1 | 9/2013 | Henon et al. | |
| 2014/0329995 A1 | 11/2014 | Johansson et al. | |
| 2016/0184737 A1 * | 6/2016 | Oscarsson | B01J 20/321 |
| | | | 210/656 |

FOREIGN PATENT DOCUMENTS

| | | |
|---|---|---|
| CN | 103450328 A | 12/2013 |
| CN | 104475041 A | 4/2015 |
| CN | 105418730 A | 3/2016 |
| JP | 2011105679 A | 6/2011 |
| JP | 2014161831 A | 9/2014 |
| KR | 20150073282 A | 7/2015 |

(Continued)

OTHER PUBLICATIONS

Peuker, U.A. et al. Bioseparation, magnetic particle adsorbents. Chapter 13. In: Downstream Industrial Biotechnology. Copyright 2013. John Wiley & Sons, Inc. Ed.: M.C. Flickinger, pp. 201-220; specif. pp. 203, 204, 206, 210, 216, 217.*

(Continued)

*Primary Examiner* — Renee Claytor
*Assistant Examiner* — Sharon M. Papciak
(74) *Attorney, Agent, or Firm* — Eversheds Sutherland (US) LLP

(57) ABSTRACT

A separation system, a method in a separation system and an elution arrangement to be provided in a separation system for separating a biomolecule from a cell culture are provided. The method comprises the steps of: —providing a feed from a cell culture (3; 103; 203) comprising said biomolecule to a magnetic separator (5; 105; 205) and providing to the magnetic separator magnetic beads comprising ligands capable of binding this biomolecule; —separating by the magnetic separator said magnetic beads with bound biomolecules from the rest of the feed; —forwarding said magnetic beads as a slurry with an added buffer to an elution cell (7; 107; 207); —eluting the bound biomolecules in the elution cell.

18 Claims, 29 Drawing Sheets

(56) References Cited

FOREIGN PATENT DOCUMENTS

| WO | WO-2006010584 A1 | * | 2/2006 | ............ B01L 3/5085 |
|----|------------------|---|--------|--------------------------|
| WO | 2006/112771 A1 | | 10/2006 | |
| WO | 2007/050017 A1 | | 5/2007 | |
| WO | 2009/102258 A1 | | 8/2009 | |
| WO | 2011059512 A1 | | 5/2011 | |
| WO | 2015/034428 A1 | | 3/2015 | |
| WO | WO-2015176018 A1 | * | 11/2015 | ........ B01L 3/502761 |

OTHER PUBLICATIONS

Ghose, S. Protein adsorption, expanded bed. Chapters. In: Downstream Industrial Biotechnology. Copyright 2013. John Wiley & Sons, Inc. Ed.: M.C. Flickinger, pp. 115-125; specif. pp. 117, 121.*
Earhart, C.M. 2010. A microfabricated magnetic sifter and high throughput physical fabrication of magnetic nanoparticles for applications in protein and cell separation. PhD dissertation. Stanford Univ. pp. 1-170; specif. pp. 5, 6.*
PCT International Search Report and Written Opinion for PCT Application No. PCT/EP2017/084620 dated May 15, 2018 (15 pages).
Great Britain Search Report for GB Application No. 1622305.9 dated Oct. 30, 2017 (7 pages).
Great Britain Search Report for GB Application No. 1622304.2 dated Nov. 9, 2017 (9 pages).
Andritz High-Gradient Magnetic Separator, 2017, 6 pages.
Ebeler et al., "One-Step Integrated Clarification and Purification of a Monoclonal Antibody Using Protein A Mag Sepharose Beads and a cGMP-Compliant High-Gradient Magnetic Separator," New Biotechnology, 2018, 42:48-55.
Flickinger, "Downstream Industrial Biotechnology; Recovery and Purification," XP055457932, 2013, 4 pages.
Franzreb et al., "Protein Purification Using Magnetic Adsorbent Particles," Appl. Microbiol. Biotechnol., 2006, 70:505-516.
GE Healthcare, 2009, "Mag Sepharose," https://www.gelifesciences.com/gehcls_images/GELS/Related%20Content/Files/1314787424814/litdoc28953763_20161014190437.pdf (2017).
Dhadge et al., "Magnetic Purification of Antibodies," 2016, https://run.unl.pt/bitstream/10362/19003/1/Dhadge_2016.pdf, 170 pages.
Safarik et al., "Magnetic Techniques for the Isolation and Purification of Proteins and Peptides," BioMagnetic Research and Technology, 2004, 2:7, pp. 1-17.
Thermo Scientific, Product Information Sheet, "Pierce Protein A/G Magnetic Agarose Beads," 2016, https://www.thermofisher.com/order/catalog/product/78609, 4 pages.
Warikoo et al., "Integrated Continuous Production of Recombinant Therapeutic Proteins," Biotechnology and Bioengineering, 2012, 109(12):3018-3029.
Japanese Office Action for JP Application No. 2019-535894 dated Sep. 13, 2021 (3 pages, with English translation of Abstract).
Cao, et al., "Immobilization *Staphylococcal* Protein A on Magnetic Cellulose Microspheres for IgG Affinity Purification," Artificial Cells, Blood Substitutes, and Biotechnology, 35:467-480, 2007.
Holschuh & Schwammle, "Preparative Purification of Antibodies with Protein A—An Alternative to Conventional Chromatography," Journal of Magnetism and Magnetic Materials, 293(1): 345-348, 2005.
Kappler, et al., "In Situ Magnetic Separation for Extracellular Protein Production," Biotechnology and Bioengineering, 102(2): 535-545, 2009.

* cited by examiner

Then repeat 4d to 4i until batch completed

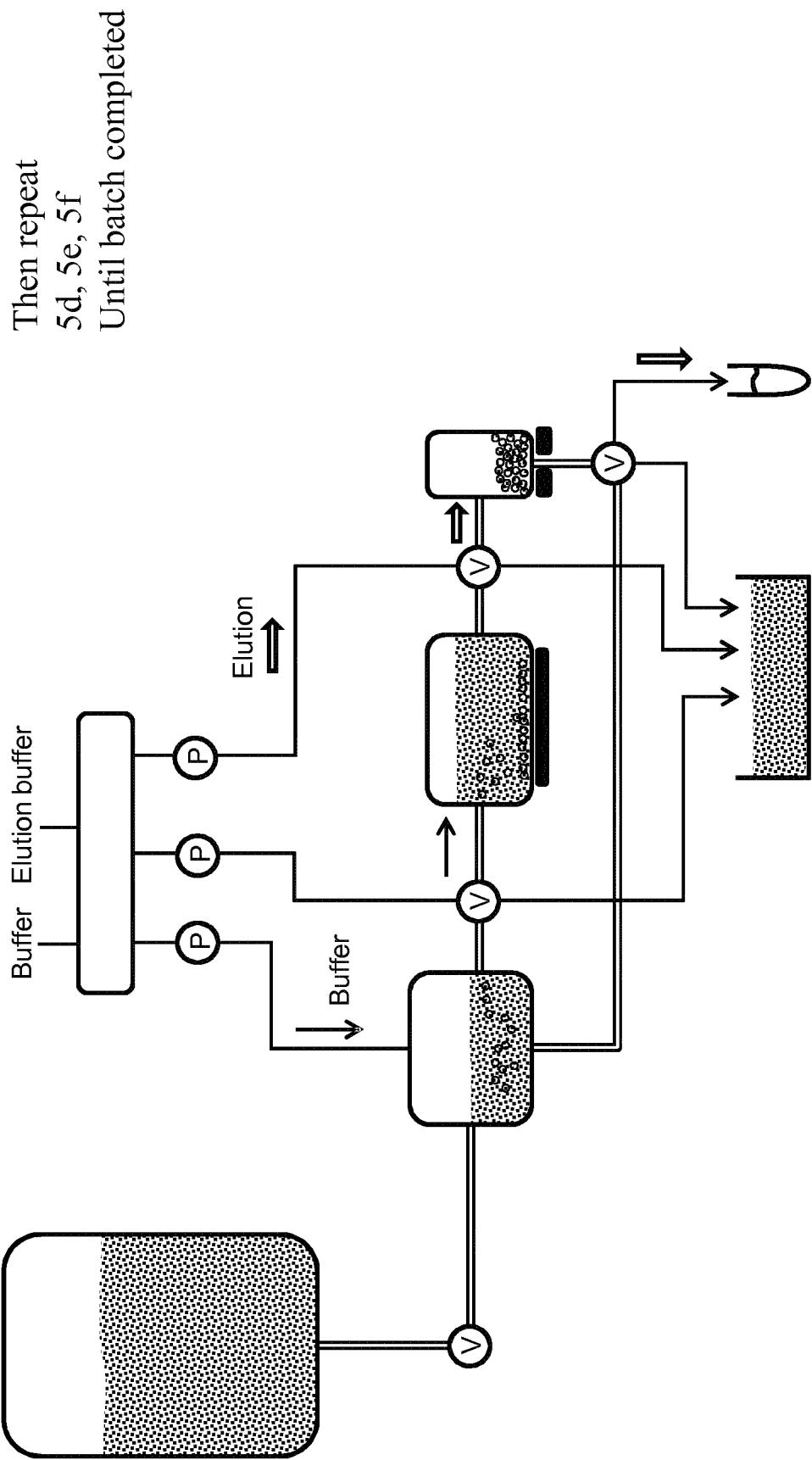

METHOD AND SYSTEM FOR SEPARATING BIOMOLECULES

CROSS REFERENCE TO RELATED APPLICATIONS

This application claims the priority benefit of PCT/EP2017/084620 filed on Dec. 27, 2017 which claims priority benefit of Great Britain Application Nos. 1622307.5, 162304.2, and 1622305.9, which were filed Dec. 28, 2016. The entire contents of which are hereby incorporated by reference herein.

TECHNICAL FIELD OF THE INVENTION

The present invention relates to a separation system and to a method in a separation system for separating a biomolecule from a cell culture

RELATED ART

Traditionally a wanted biomolecule is separated from a cell culture by first clarifying the cell culture, i.e. remove cells, other biomolecules and different rest products. The clarifying usually comprises for example ultracentrifugation, depth filtration and sterile filtration. After the clarifying step further purification is needed, for example by chromatography. This is in many ways a complicated, time consuming and expensive process.

SUMMARY

It is an object of the present invention to provide an improved method and system for separating biomolecules from a cell culture.

This is achieved in a method, system and elution arrangement according to the independent claims.

In one aspect of the invention a method in a separation system for separating a biomolecule from a cell culture is provided. The method comprises the steps of:
  providing a feed from a cell culture comprising said biomolecule to a magnetic separator and providing to the magnetic separator magnetic beads comprising ligands capable of binding this biomolecule;
  separating by the magnetic separator said magnetic beads with bound biomolecules from the rest of the feed;
  forwarding said magnetic beads as a slurry with an added buffer to an elution cell;
  eluting the bound biomolecules in the elution cell.

In another aspect of the invention a separation system for separating a biomolecule from a cell culture is provided. Said system comprises:
  a magnetic separator comprising an inlet for receiving a feed from the cell culture comprising said biomolecule and for receiving magnetic beads comprising ligands capable of binding this biomolecule, said magnetic separator being configured for separating said magnetic beads with said bound biomolecule from the rest of the feed; and
  an elution arrangement comprising an elution cell, said elution cell comprising an elution cell inlet in connection with an outlet from the magnetic separator for receiving said separated magnetic beads as a slurry with buffer from the magnetic separator, wherein said elution arrangement is configured for eluting the biomolecule from the magnetic beads.

In further another aspect of the invention an elution arrangement configured for being connected in a separation system as described above is provided. Said elution arrangement comprises an elution cell, said elution cell comprising an elution cell inlet configured for being connected to an outlet from a magnetic separator for receiving magnetic beads as a slurry with buffer from the magnetic separator, wherein said elution arrangement is configured for eluting a biomolecule from the magnetic beads.

Hereby a more effective method and system for separating biomolecules are achieved. The separation process is much easier, faster and cheaper than traditional separation processes. When cells and solid contaminants are separated from the magnetic beads in the magnetic separator, the beads are transferred to a separate elution arrangement with low dead volume to facilitate high concentration and low elution volume of target biomolecule. The system including an elution arrangement and easy transport and capture of the magnetic beads will increase the effectivity of the system since two or more separation processes can be run in parallel.

A closed and aseptic system is possible and two or three separation processes can be run in parallel in the system. The magnetic beads can be reused for a next separation cycle. The elution can be performed in a smaller volume than in the magnetic separator which will improve effectivity. A batch uptake of biomolecule will give a more homogenous uptake of target onto the beads in comparison to traditional chromatography. In traditional chromatography, the concentration of the target is high at the inlet of the column and aggregate formation of target may occur. If the target is evenly distributed on the resin bed there is a lower risk for aggregation and precipitation at elution.

In one embodiment of the invention the magnetic beads are forwarded from the elution cell for reuse in the magnetic separator.

In one embodiment of the invention a new portion of feed from the cell culture and magnetic beads are provided into the magnetic separator while a previous portion is in the elution cell, whereby at least two portions of magnetic beads are circulating in the separation system. Hereby an effective process is achieved.

Further embodiments are described in the dependent claims.

BRIEF DESCRIPTION OF THE DRAWINGS

FIG. 3a is a flow chart of a method for separating a biomolecule in the system shown in FIG. 1a.
FIGS. 5, 5a-5f show schematically a separation system according to one embodiment of the invention.

DETAILED DESCRIPTION OF EMBODIMENTS

According to the invention a method and a separation system for separating a biomolecule from a cell culture is provided. Furthermore, an elution arrangement configured for being connected to a separation system is provided. The method comprises the steps of:

- providing a feed from a cell culture comprising said biomolecule to a magnetic separator and providing magnetic beads comprising ligands capable of binding this biomolecule to the magnetic separator;
- separating by the magnetic separator said magnetic beads with bound biomolecules from the rest of the feed;
- forwarding said magnetic beads as a slurry with an added buffer to an elution cell;
- eluting the bound biomolecules in the elution cell.

In some embodiments, the method further comprises forwarding the magnetic beads from the elution cell for reuse in the magnetic separator.

Figure 1A:
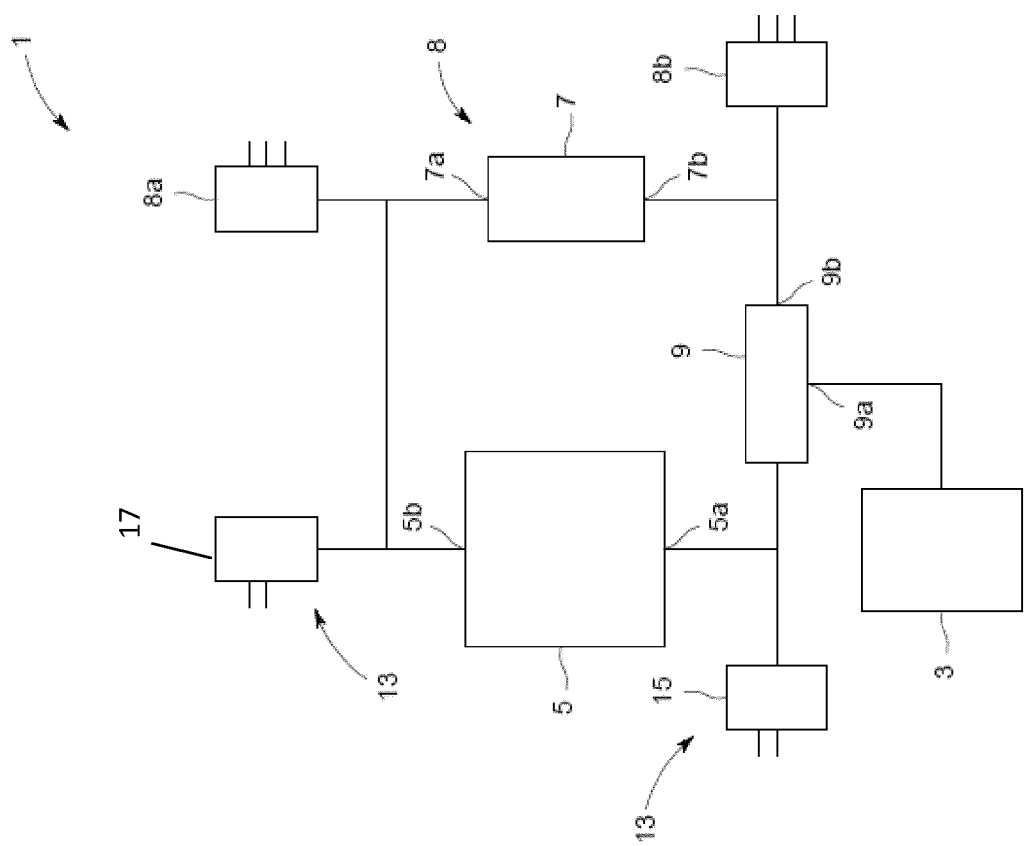
FIG. 1a shows schematically a separation system according to one embodiment of the invention.
Figure 1B:
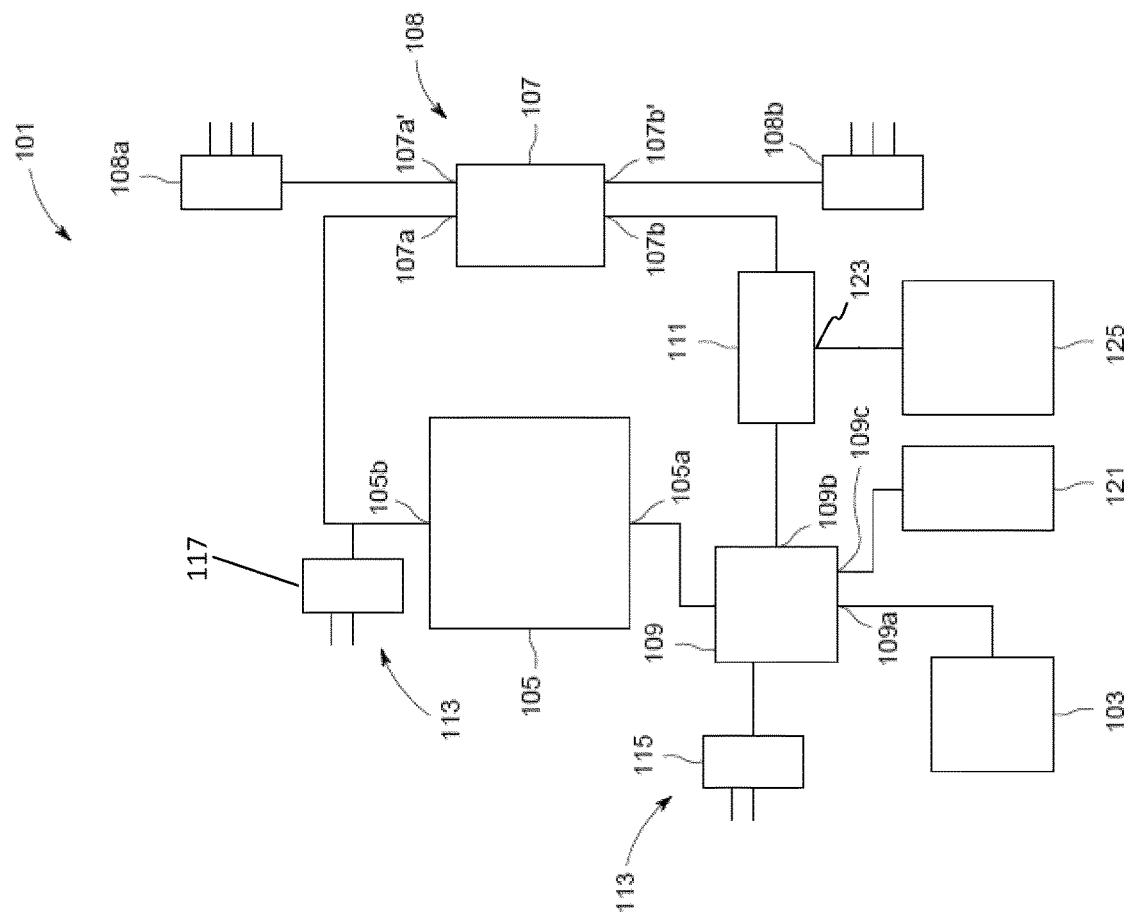
FIG. 1b shows schematically a separation system according to another embodiment of the invention.
Figure 1C:
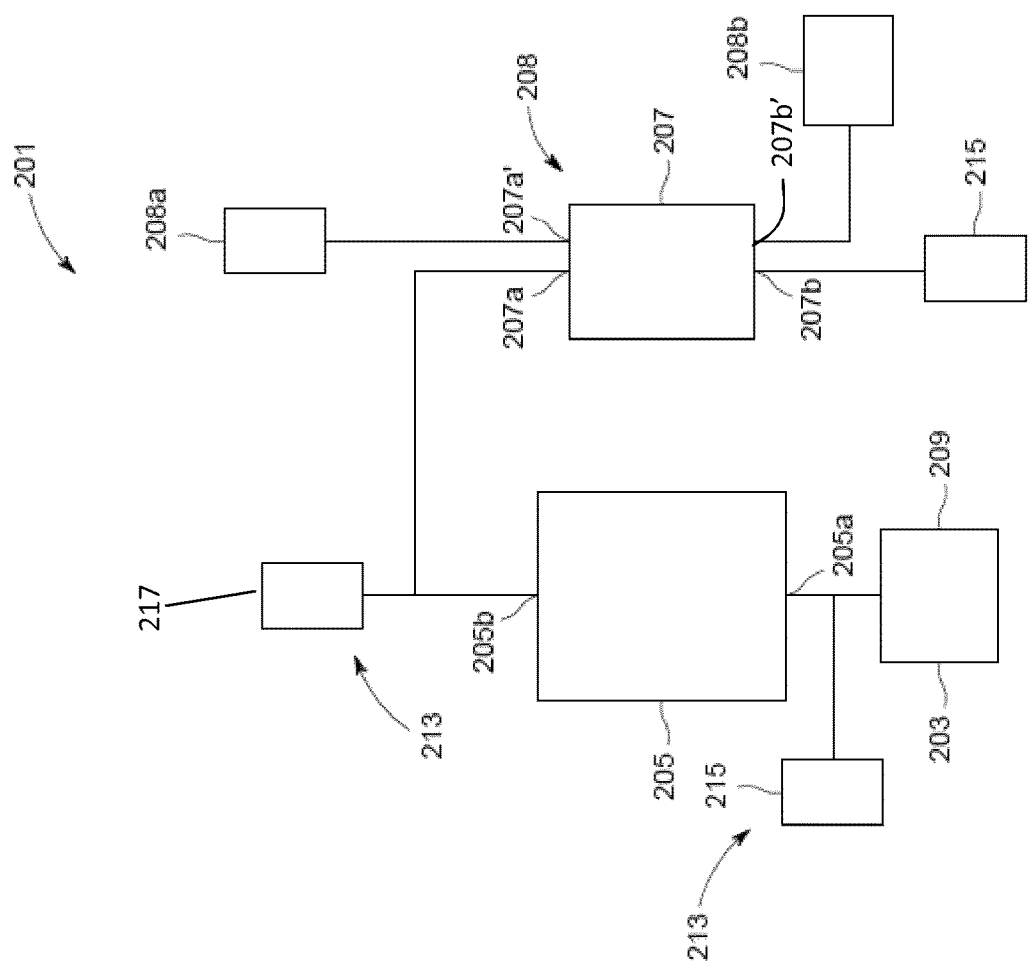
FIG. 1c shows schematically a separation system according to another embodiment of the invention.

FIGS. 1a, 1b and 1c show schematically three different possible separation systems 1, 101, 201 according to the invention. Some features are the same and will be described only once and some features in one of the systems can also be used in one of the other systems. Common for the three shown systems 1, 101, 201 is that they comprise a magnetic separator 5, 105, 205. This could e.g. be a high gradient magnetic separator as described in U.S. Pat. No. 7,506,765, hereby incorporated by reference in its entirety. A magnetic separator separates magnetic particles from a fluid. The magnetic separator 5; 105; 205 comprises an inlet 5a; 105a; 205a for receiving a feed from a cell culture 3; 103; 203 comprising said biomolecule and for receiving magnetic beads comprising ligands capable of binding this biomolecule. The magnetic separator 5; 105; 205 is configured for separating said magnetic beads with said bound biomolecule from the rest of the feed. The magnetic separator 5; 105; 205 comprises parts of magnetic material inside the magnetic separator which parts attract the magnetic beads when a magnetic field is applied. The magnetic separator is configured for releasing the magnetic field when the magnetic beads are to be forwarded to an elution cell 7; 107; 207 provided outside the magnetic separator and connected to the magnetic separator. The magnetic separator further comprises a washing arrangement 13; 113; 213 configured for washing out other components from the magnetic separator 5; 105; 205 than those magnetically bound to the parts of magnetic material. The washing arrangement 13; 113; 213 comprises at least one wash buffer providing arrangement 15; 115; 215 connected to a pump and to the inlet 5a; 105a; 205a of the magnetic separator possibly via a capturing cell 9; 109; 209 and a wash buffer collection arrangement 17; 117; 217 connected to an outlet 5b; 105b; 205b of the magnetic separator. The washing arrangement 13; 113; 213 is configured for flowing washing buffer through the magnetic separator 5; 105; 205 for washing out other components of the feed than those bound to the magnetic parts.

All three separation systems 1; 101; 201 also comprises an elution arrangement 8; 108; 208 comprising an elution cell 7; 107; 207. The elution cell comprises an elution cell inlet 7a; 107a; 207a, in connection with an outlet 5b; 105b; 205b from the magnetic separator 5; 105; 205 for receiving said separated magnetic beads as a slurry with buffer from the magnetic separator. When forwarding said magnetic beads from the magnetic separator 5; 105; 205 to the elution arrangement buffer is suitably added to the magnetic separator for allowing the magnetic beads to be flowed to the elution arrangement 8; 108; 208.

The elution arrangement 8; 108; 208 is configured for eluting the biomolecule from the magnetic beads. Hereby the elution arrangement 8; 108; 208 comprises a buffer providing arrangement 8a; 108a; 208a connected to an elution cell inlet 7a; 107a'; 207a' and a collection arrangement 8b; 108b; 208b connected to an elution cell outlet 7b; 107b'; 207b'. The elution arrangement is configured for performing elution by providing elution buffer from the buffer providing arrangement and collecting eluate in the collection arrangement and possibly also performing strip and cleaning in place, CIP, by providing cleaning buffer from the buffer providing arrangement and collect waste in the collection arrangement and possibly also performing equilibration of the magnetic beads in the elution cell by providing equilibration buffer from the buffer providing arrangement. In some embodiments the elution cell 107, 207 comprises two inlets 107a, 107a'; 207a, 207a' and two outlets 107b, 107b'; 207b, 207b'. Actually, also the elution cell 7 in the separation system shown in FIG. 1a can have two inlets and two outlets instead of only one inlet and one outlet and valves directing the fluids. And correspondingly the elution cells of the separation systems shown in FIGS. 1b and 1c could have only one inlet and one outlet as shown in FIG. 1a.

In the embodiment shown in FIG. 1b the elution cell 107 comprises an elution cell first outlet 107b for forwarding the magnetic beads for reuse in the magnetic separator 105 and an elution cell second outlet 107b' for collecting eluate and waste in a collection arrangement 108b.

In the embodiment shown in FIG. 1c the elution cell 207 comprises an elution cell first outlet 207b for forwarding the magnetic beads to a storage vessel 215 and an elution cell second outlet 207b' for collecting eluate and waste in a collection arrangement 208b. The separation system 201 shown in FIG. 1c is a system without a circulation and reuse of the magnetic beads. In this system, a cell culture 203 can be provided with the magnetic beads and connected to the separation system 201. Possibly all the content of the cell culture 203 could be provided to the magnetic separator 205. The magnetic beads are retrieved in the storage vessel 215 after the eluting of the biomolecules in the elution cell 207.

The elution cell 107; 207 comprises in the embodiment shown in FIGS. 1b and 1 an elution cell first inlet 107a; 207a for receiving magnetic beads from the magnetic separator 105; 205 and an elution cell second inlet 107a'; 207a' for receiving elution buffer, cleaning in place, CIP, buffer and equilibration buffer from a buffer providing arrangement 108a; 208a.

The elution cell 7; 107; 207 comprises a retaining arrangement 502a-c,f-h for keeping the magnetic beads within the elution cell and allowing excess buffer to escape from the elution cell. These retaining arrangement and further details of the elution cells are shown in FIGS. 2a-2e and described further below.

In the embodiments shown in FIGS. 1a and 1b an elution cell outlet 7b; 107b is configured for forwarding the magnetic beads from the elution cell for reuse in the magnetic separator 5; 105; 205.

The separation systems 1; 101 shown in FIGS. 1a and 1b comprises a capturing cell 9; 109 which is connected to the inlet 5a; 105a of the magnetic separator 5; 105. The cell culture 203 in the embodiment shown in FIG. 1c can also be called a capturing cell 209 if magnetic beads are added to the cell culture 203. Another alternative would be to add magnetic beads directly to the magnetic separator 5; 105; 205 instead. Separate addition of cell culture and magnetic beads directly into the magnetic separator is possible for all the embodiments and should be covered by this invention.

The capturing cells 9; 109 shown in FIGS. 1a and 1b comprises a cell culture inlet 9a; 109a for receiving a feed from a cell culture 3; 103 and at least one magnetic bead inlet 9b; 109b; 109c for receiving magnetic beads. The capturing cell 9; 109 is configured for mixing the feed from the cell culture and the magnetic beads thus allowing the specific biomolecule to bind to the magnetic beads before forwarding it to the magnetic separator 5; 105.

In the separation systems 1; 101; 201 according to the invention a new portion of feed from the cell culture 3; 103; 203 and magnetic beads can be provided into the magnetic separator 5; 105; 205 while a previous portion is in the elution cell 7; 107; 207. Hereby at least two portions of magnetic beads can be used in the separation system simultaneously and processes for separating biomolecules can be made more effective.

In the embodiments shown in FIGS. 1a and 1b the magnetic beads are circulating in the separation system 1; 101 and still a new portion of feed from the cell culture 3; 103 and magnetic beads can be provided into the magnetic separator 5; 105 while one previous portion is in the elution cell 7; 107 and one previous portion is in a capturing cell 9; 109. Hereby three portions of magnetic beads are circulating in the separation system 1; 101; 201.

For all the embodiments shown in FIGS. 1a-1c the cell culture 3; 103; 203, the magnetic separator 5; 105; 205 and the elution arrangement 8; 108; 208 can be connected by pre-sterilized, flexible tubing and aseptic connectors. Furthermore, the elution cell can be pre-sterilized and disposable. A closed and sterile separation system for single use can hereby be provided.

The separation system 101 shown in FIG. 1b comprises further an intermediate cell 111 connected to an elution cell outlet 107b and configured for receiving the magnetic beads form the elution cell. The intermediate cell 111 is configured for forwarding the magnetic beads for possible reuse in the magnetic separator 5; 105; 205. The intermediate cell 111 comprises in one embodiment a draining arrangement for removing excess buffer from the intermediate cell 111. Such a draining arrangement could also or instead be provided to the capturing cell 9, 109 of the systems in FIGS. 1a and 1b.

In some embodiments, the draining arrangement in the intermediate cell 111 is constructed as the retaining arrangement 502 b-c, f, h and comprises a magnet for keeping the magnetic beads inside the intermediate cell 111 by magnetic force while draining the intermediate cell from buffer.

In another aspect of the invention an elution arrangement 8; 108; 208 is provided which is configured for being connected in a separation system as described above.

FIGS. 2a-2h show schematically different elution cells 307a-h according to different embodiments of the invention. Any of the elution cells 307a-h shown in FIGS. 2a-2h can be used as elution cell 7; 107; 207 in the systems shown in FIGS. 1a-1c and as elution cell, EC, as shown in the FIGS. 4 and 5.

Figure 2B:
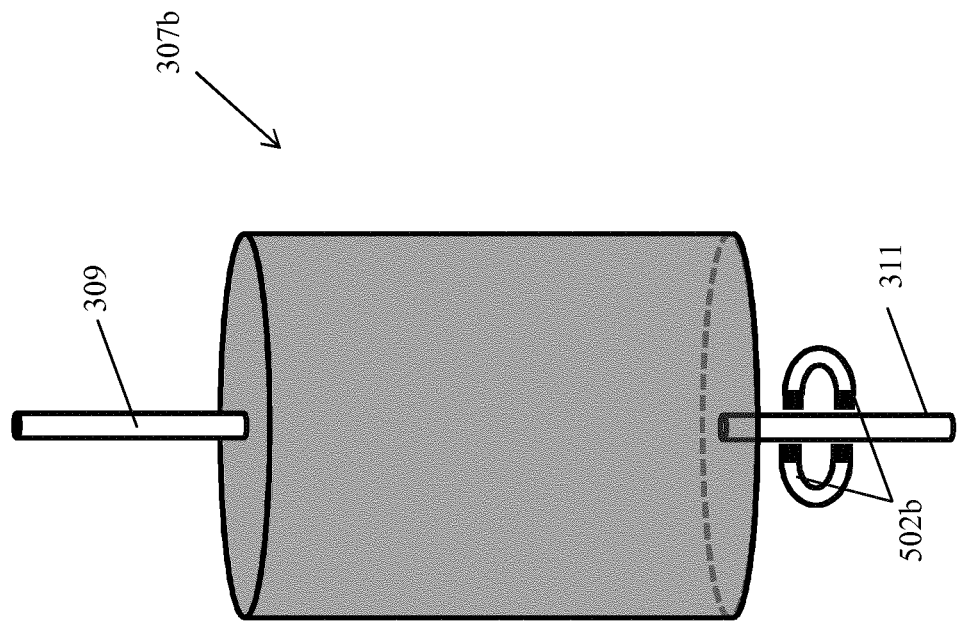
FIGS. 2a-2h show schematically an elution cell according to different embodiments of the invention.
Figure 2A:
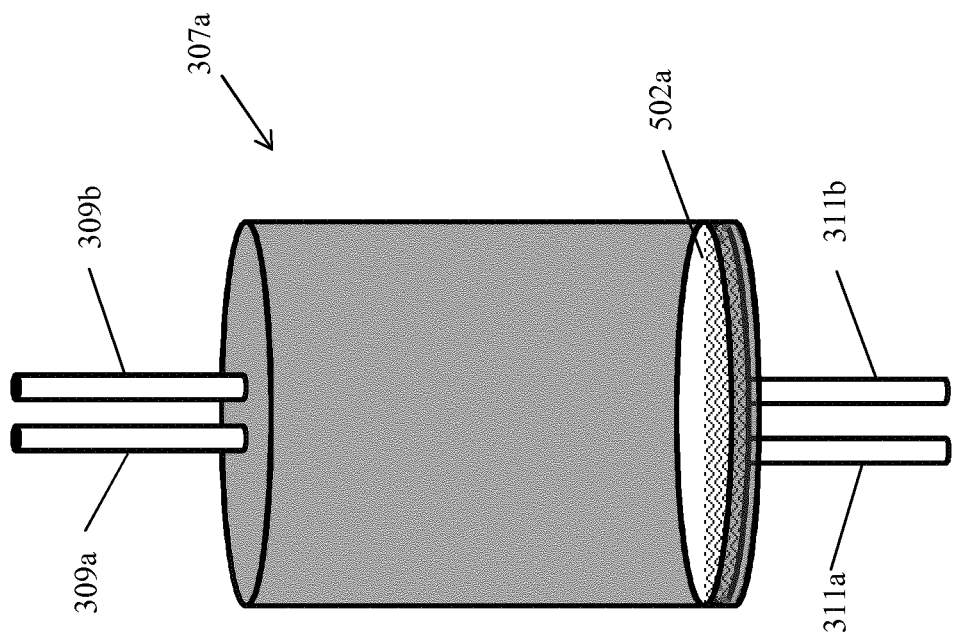
Figure 2D:
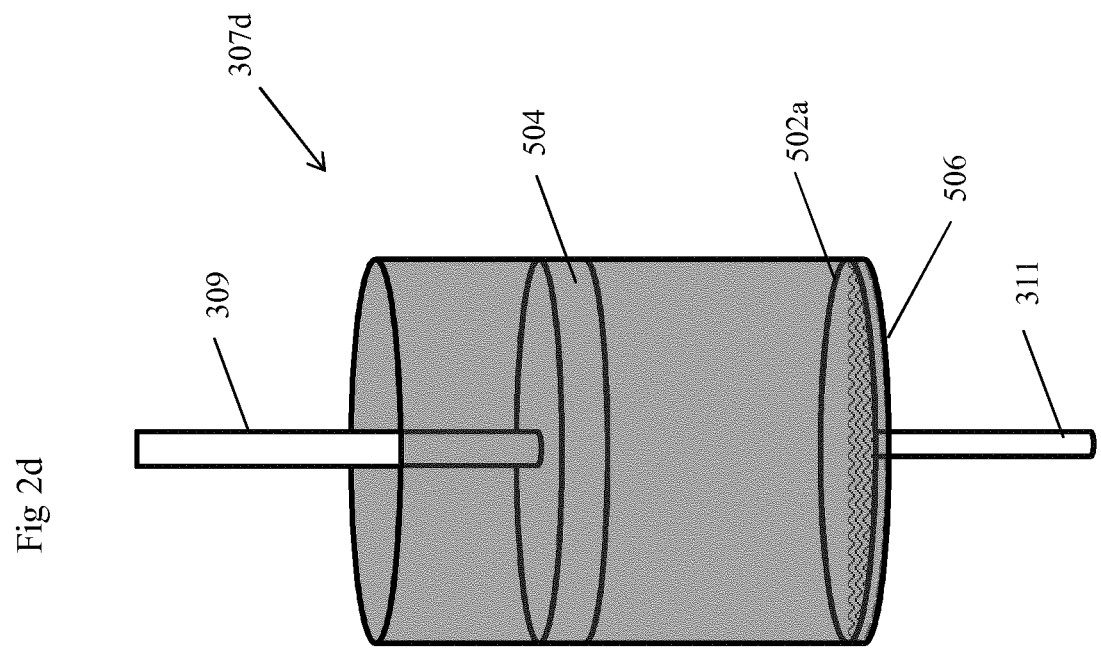

FIG. 2a shows an elution cell 307a. This elution cell 307a has an inner compartment for housing the magnetic beads coming from the magnetic separator. The elution cell 307a comprises a first inlet 309a for receiving the magnetic beads from the magnetic separator. The elution cell 307a comprises further a second inlet 309b for receiving buffer, such as elution buffer, CIP buffer and equilibration buffer from a buffer providing arrangement 8a, 108a, 208a as described above. The elution cell 307a comprises further in this embodiment a first outlet 311a for forwarding the magnetic beads, possibly for reuse as described above. The elution cell 307a comprises further a second outlet 311b connected to a collection arrangement 8b; 108b; 208b as described above. In another embodiment one single inlet and one single outlet to the elution cell could be provided and valves connected to the inlet and outlet for directing buffer and magnetic beads correctly. All the elution cells 307a-h described in relation to FIGS. 2a-h can be provided with either one or two inlets and outlets even if only the elution cells 307a and 307g as disclosed in FIGS. 2a and 2g are shown with two inlets and two outlets.

The volume of the elution cell 307a can either be of a size such that all the content received from the magnetic separator, i.e. magnetic beads and buffer, called slurry of magnetic beads, can fit into the elution cell or the volume can be smaller. If the elution cell 307a has a smaller volume the magnetic beads can be packed in the elution cell by flow packing, i.e. flowing the slurry of magnetic beads through the elution cell 307a. A retaining arrangement 502a needs to be provided in the elution cell 307a for keeping the magnetic beads within the elution cell 307a while allowing the buffer to escape out from the elution cell. The retaining arrangement 502a can be a for example a filter, also called a frit or a sinter provided such that it covers the outlets 311a, 311b from the elution cell 307a. Another possible retaining arrangement could be a pinch valve just pinching the outlet(s) or a magnetic force provided to the outlet(s) or to a part of the elution cell close to the outlet(s). If the internal volume of the elution cell is smaller than the total volume of slurry of magnetic beads to be received from the magnetic separator the volume of the elution cell can in one embodiment of the invention be less than half the volume of the total amount of the slurry of the magnetic beads to be received. Hereby the flow packing will provide a bed of magnetic beads within the elution cell with a suitable void volume, for example less than 60%. If on the other hand the elution cell 307a has a larger internal volume arranged for comprising all the received slurry of magnetic beads for example gravitational force or magnetic force could be used for providing a packed bed of magnetic beads suitable for the elution process. Magnetic force could be provided to a part of the elution cell close to the outlet, as for example shown in FIG. 2f. Optionally a distribution system for distributing buffer in the elution cell can be provided to both inlet and outlet or only the inlet in all of the embodiments shown in FIGS. 2a-2h, however this is not shown.

In FIG. 2b a similar elution cell 307b as the one disclosed in FIG. 2a is shown. However, in this elution cell 307b only one inlet 309 and one outlet 311 is provided. As described above two inlets and two outlets could as well be provided in this embodiment of the elution cell 307b. In this embodiment of the elution cell 307b a retaining arrangement 502b in the form of a magnetic force is provided. A magnet which can be turned on and off is provided around the outlet 311 of the elution cell 307b or around a part of the elution cell close to the outlet 311.

The magnetic beads will be kept inside the elution cell 307b when the magnetic force is applied and buffer can escape through the magnetic beads. Hereby a bed of magnetic beads is packed. This could be done as described above and depending on the size of the internal volume of the elution cell 307b, i.e. for example flow packing, gravitational packing or packing by using the magnetic force form the retaining arrangement 502b.

Figure 2C:
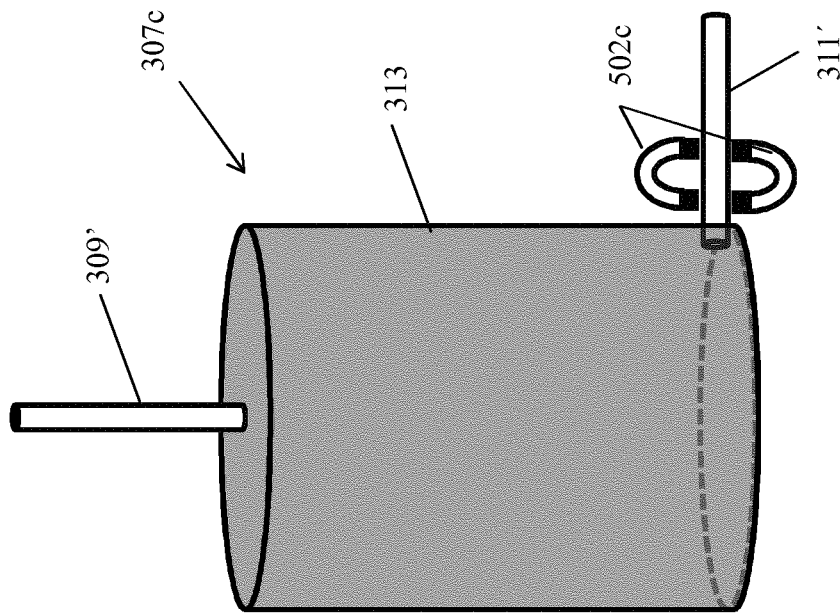
Figure 2F:
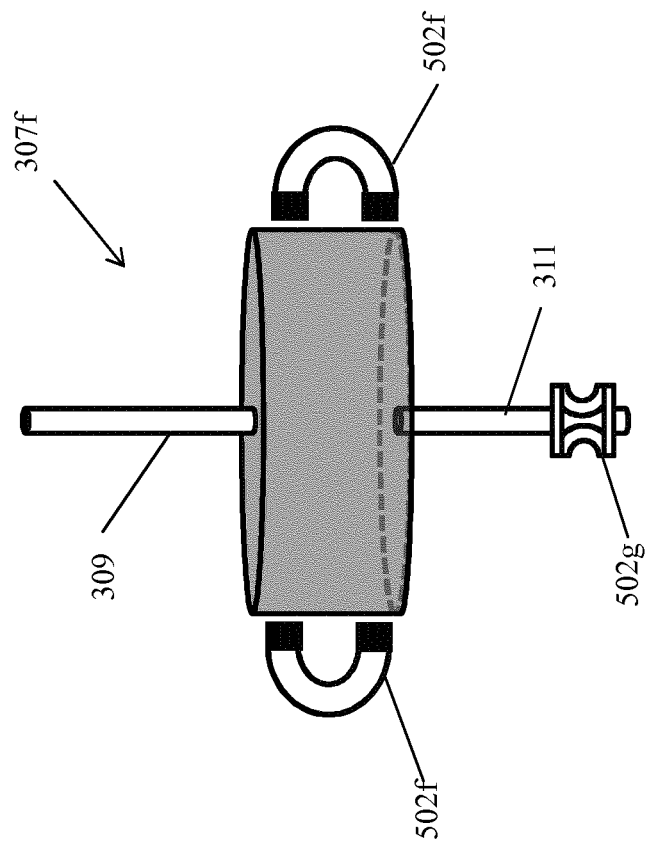

In FIG. 2c another embodiment of an elution cell 307c according to the invention is shown. Also this embodiment comprises only one inlet 309' and one outlet 311' however two inlets and two outlets could instead be provided as discussed above. The outlet 311' is in this embodiment provided in a lower part of a side wall 313 of the elution cell 307c. Where lower refers to the directions in the drawings and an opposite side to where the inlet 309' is provided. In the previously described embodiments shown in FIGS. 2*a* and 2*b* the outlet is instead provided in a bottom of the elution cell 307*a*, 307*b*. A retaining arrangement 502*c* is provided to the outlet 311', here shown in the form of a magnetic force. However also in this embodiment a filter or a pinch valve could instead be provided. The size of the elution cell 307*c* and the methods of packing the magnetic beads correspond to the previously described embodiments as described in relation to FIGS. 2*a* and 2*b*.

FIG. 2*d* shows another embodiment of an elution cell 307*d* according to the invention. One inlet 309 and one outlet 311 as in FIG. 2*b* are shown however also two inlets and two outlets could be provided. A retaining arrangement 502*a* in the form of a filter as in FIG. 2*a* is provided covering the outlet 311. In this embodiment, an adaptor 504 is also provided inside the elution cell 307*d*. The adaptor is initially provided in a start position which is close to the inlet 309 of the elution cell 307*d*. The internal volume of the elution cell is defined by the inner walls of the elution cell 307*d* and the adaptor. The slurry of magnetic beads is provided into the elution cell 307*d* and the packing of the magnetic beads is provided by forcing the adaptor towards the outlet 311 of the elution cell 307*d*. Buffer will escape through the retaining arrangement 502*a* and the outlet 311. The adaptor is stopped when a suitable packed bed is achieved. This could be for example a void volume less than 60%. In another embodiment, the inlet is provided in a bottom of the elution cell and the outlet in the top and an adaptor can be provided from the bottom of the elution cell instead of as shown in FIG. 2*d* from the top.

Figure 2E:
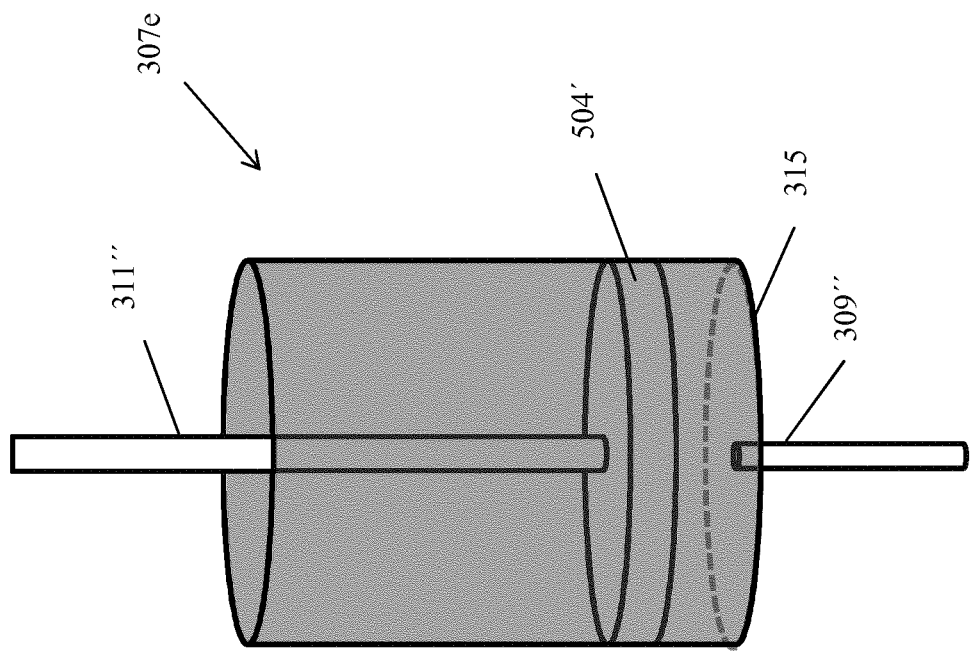
Figure 2G:
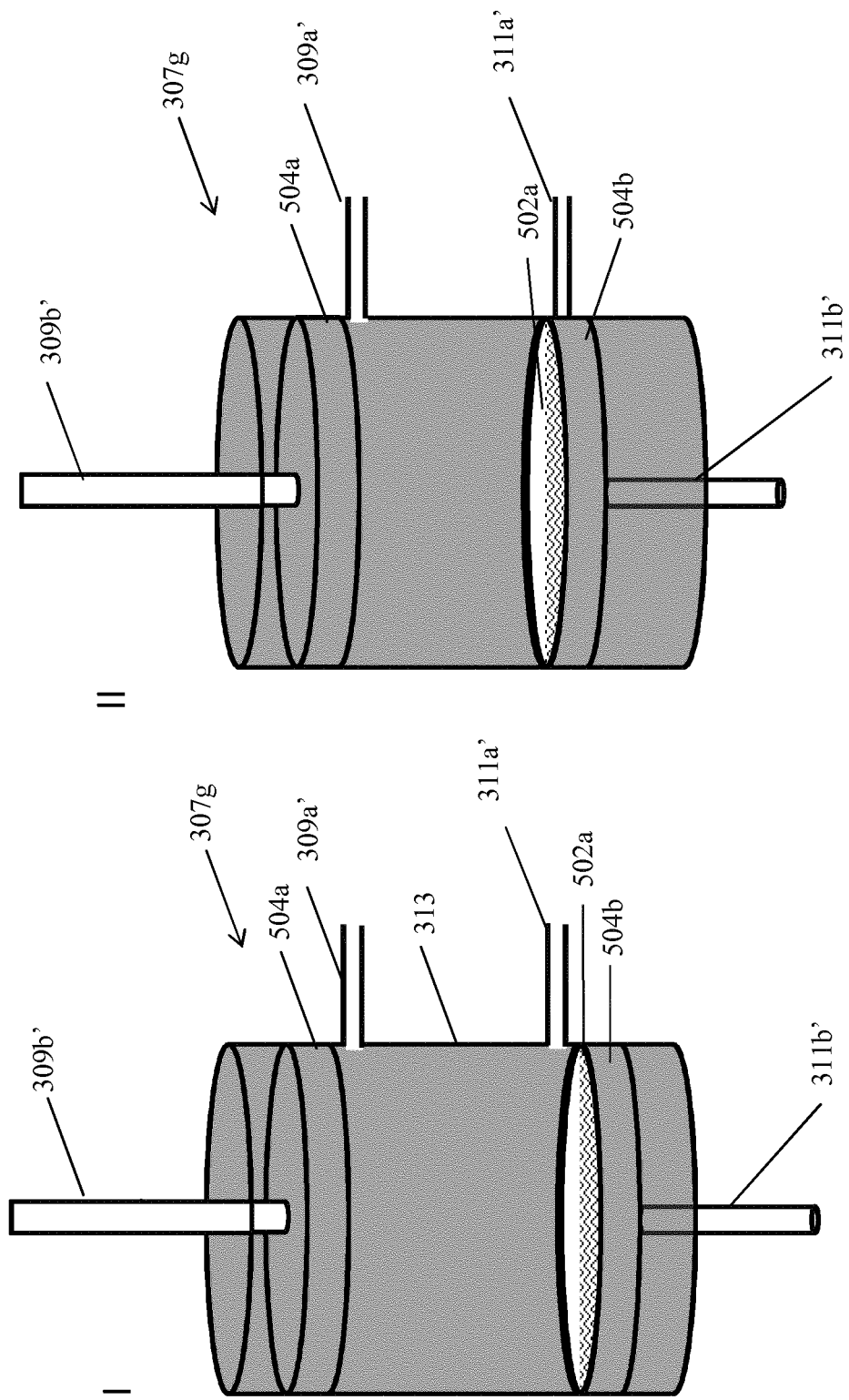
Figure 2G:
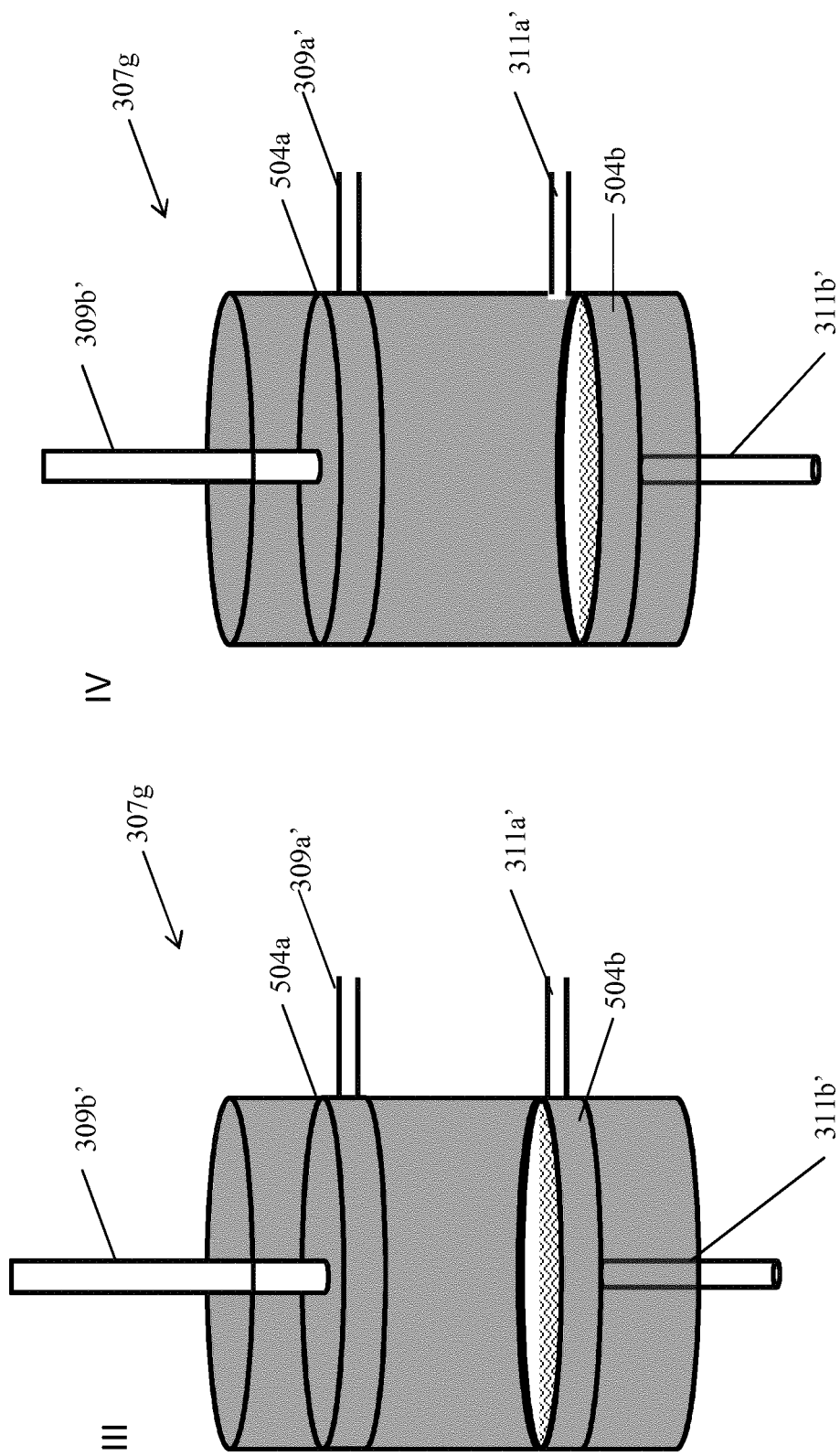

FIG. 2*e* shows another embodiment of an elution cell 307*e* according to the invention. In this embodiment, an inlet 309" is provided in a bottom 315 of the elution cell 307*e* instead of in a top as in the previously described embodiments. An outlet 311" is provided in the other end of the elution cell 307*e*. As discussed before two inlets and two outlets could be provided also in this embodiment. An adaptor 504' is provided inside the elution cell 307*e* and defines the internal volume of the elution cell 307*e* together with the bottom 315 and the inner side walls of the elution cell. In this embodiment buffer can escape through the adaptor 504' but the magnetic beads will be kept between the inlet 309" and the adaptor 504'. By flowing the slurry of magnetic beads into the elution cell 307*e* and by providing a suitable force towards the flow from the adaptor 504' a packed bed of magnetic beads can be achieved having a suitable void volume. The force provided to the adaptor 504' can be varied. A retaining arrangement such as a pinch valve could be provided to the inlet 309".

FIG. 2*f* shows another embodiment of an elution cell 307*f* according to the invention. In this embodiment, a wide and short elution cell is provided. Hereby a short bed of magnetic beads will be provided. This gives a lower pressure during elution and increased flow and hereby a faster elution. One inlet 309 is shown in a top of the elution cell 307*f* and one outlet 311 is shown in a bottom of the elution cell. A retaining arrangement 502*f* is provided in the form of a magnetic force which is applied to a part of the elution cell side walls and not only to the outlet. Hereby the magnetic force is used also for the packing of the magnetic beads as described above. An extra retaining arrangement 502*g* in the form of a pinch valve is also shown provided to the outlet 311.

FIG. 2*g* shows another embodiment of an elution cell 307*g* according to the invention. In this embodiment, the elution cell 307*g* comprises a first inlet 309*a*' for receiving the magnetic beads from the magnetic separator provided in a side wall 313 of the elution cell 307*g*. The elution cell 307*g* comprises further a second inlet 309*b*' for receiving buffer, such as elution buffer, CIP buffer and equilibration buffer from a buffer providing arrangement 8*a*, 108*a*, 208*a* as described above. The second inlet 309*b*' is provided through a movable first adaptor 504*a*. The elution cell 307*g* comprises further in this embodiment a first outlet 311*a*' for forwarding the magnetic beads, possibly for reuse as described above. The first outlet 311*a*' is also provided in a side wall 313 of the elution cell 307*g*. The elution cell 307*g* comprises further a second outlet 311*b*' connected to a collection arrangement 8*b*; 108*b*; 208*b* as described above. The second outlet 311*b*' is provided through a second movable adaptor 504*b*. An inner volume of the elution cell 307*g* for housing the magnetic beads is defined by the side wall 313 and the first and second adaptors 504*a*, 504*b*. Both the first and second adaptors 504*a*, 504*b* can be provided with a retaining arrangement 502*a*, such as a filter, frit or sinter. Furthermore, both the first and second adaptors 504*a*, 504*b* can be provided with a distribution system for distributed sample providing and collection. However, this may not be necessary. FIG. 2*g* shows four different positions of the movable adaptors, I, II, III, IV. In the first position, I, both the first and second adaptors 504*a*, 504*b* are in retracted positions, i.e. providing a maximum inner volume of the elution cell 507*g*. In this position, the first adaptor 504*a* is provided above (referring to directions in the drawings) the first inlet 309*a*'—hereby the first inlet 309*a*' has access to an internal volume of the elution cell. In this first position, also the second adaptor 504*b* is provided below (referring to directions in the drawings) the first outlet 311*a*' and hereby the first outlet 311*a*' has access to the internal volume of the elution cell. Hereby the internal volume of the elution cell, also called a chamber, is open for rinse. In a second position, II, the chamber is provided in a position for trapping magnetic beads. A slurry of magnetic beads is received through the first inlet 309*a*' from the magnetic separator. A bed of magnetic beads is built up on retaining arrangement 502*a* provided to the second adaptor 504*b* and buffer will pass through the retaining arrangement 502*a* and out from the elution cell 307*g* through the second outlet 311*b*'. In the third position, III, the chamber is in a closed position. The first adaptor 504*a* has been moved down below the first inlet 309*a*' (referring to the directions in the drawing). The elution cell 307*g* is now in a closed position and possibly also in a compressed position. Possibly the first adaptor 504*a* compressed a bed of magnetic beads when moving down. However, elution could also be performed in an open bed. In the third position the elution cell is now ready for elution, strip, CIP and equilibration as described above. In a fourth position, IV, the second adaptor 504*b* has been retracted again thus opening up the chamber for the first outlet 311*a*'. Hereby the elution cell 307*g* is now ready for forwarding of the magnetic beads possibly for reuse as described above. The magnetic beads could be flushed out by adding extra buffer and/or pressed out by using the first adaptor 504*a*.

Figure 2H:
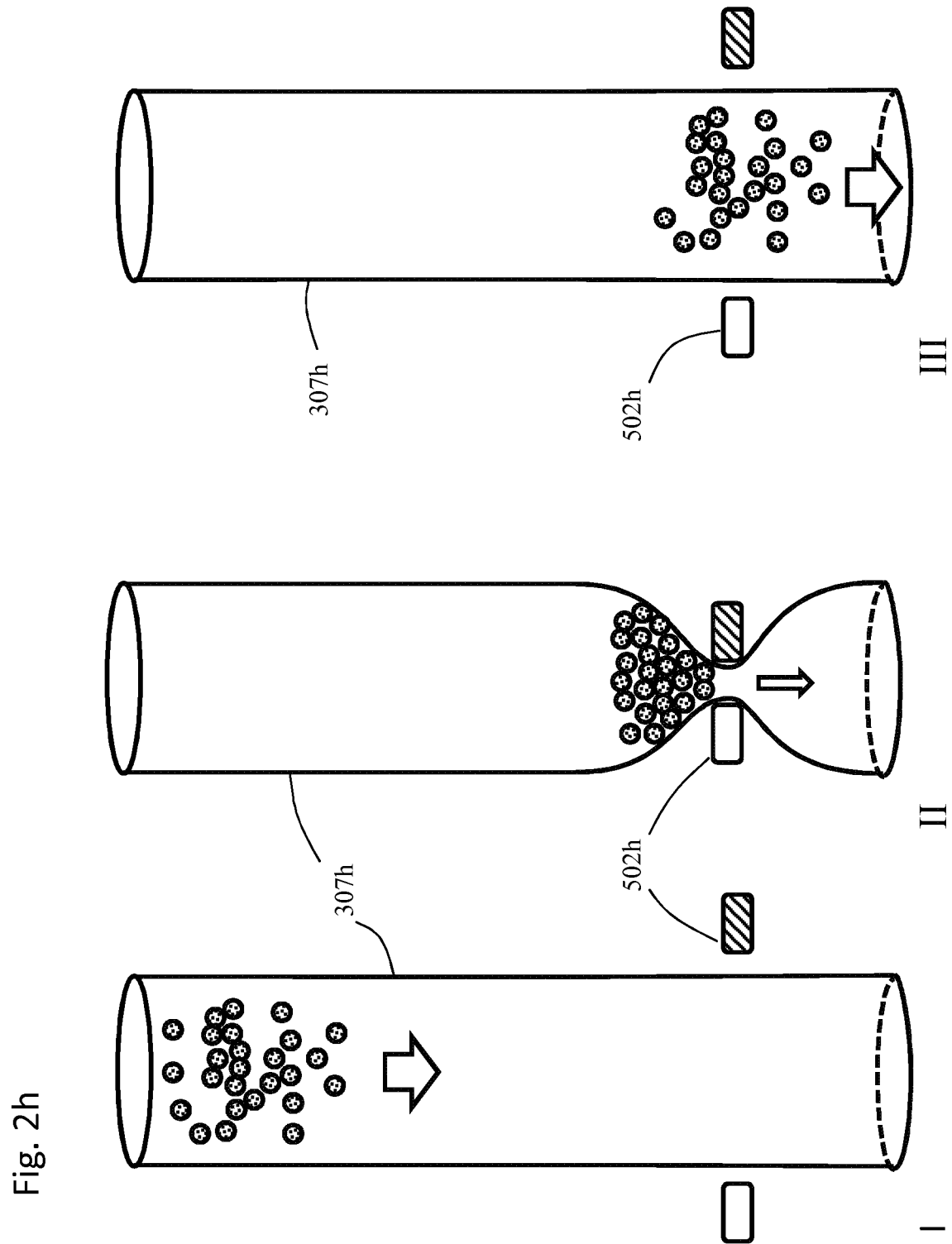

FIG. 2*h* shows another embodiment of an elution cell 307*h* according to the invention in three positions, I, II, III. In this embodiment, the elution cell 307*h* is a flexible tube, possibly larger than the rest of the tubing in the system. It is here shown how the elution could be performed in the flexible tube itself by providing a retaining arrangement 502*h* in the form of a pinch valve with or without a magnetic component. The retaining arrangement 502*h* can compress a part of the elution cell 307*h* for collecting magnetic beads provided from the magnetic separator while letting buffer pass. Elution and possibly CIP, strip and equilibration can be performed and then the retaining arrangement 502*h* could be released for forwarding the magnetic beads possibly for reuse as discussed above.

Figure 3A:
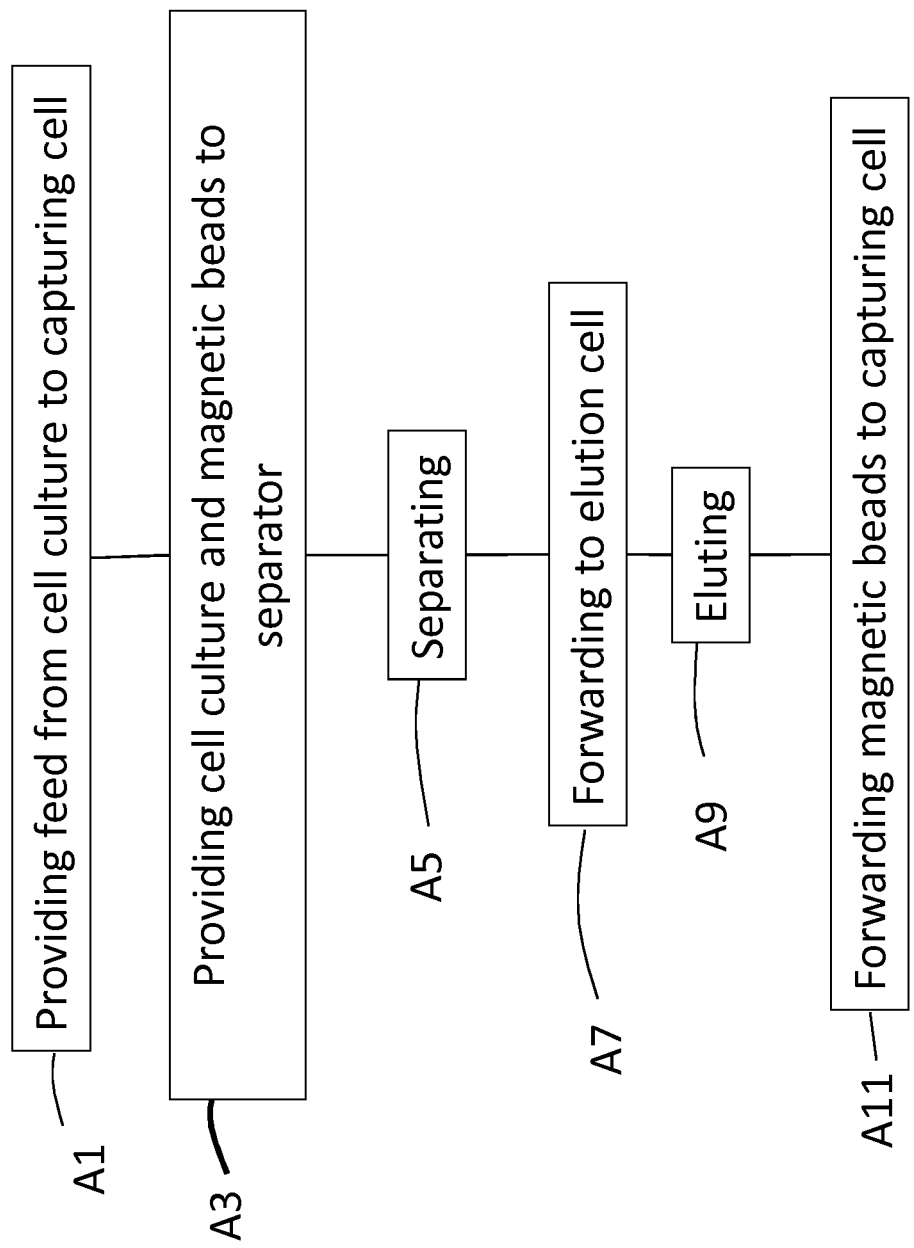

FIG. 3*a* is a flow chart of a method for separating a biomolecule in the system shown in FIG. 1*a*. The steps of the method are described in order below:

A1: Providing a feed from a cell culture 3 to a capturing cell 9. Said feed comprises a biomolecule to be separated. Said capturing cell 9 comprises magnetic beads comprising ligands capable of binding this biomolecule. In the capturing cell 9 the biomolecule will bind to the magnetic beads. Possibly mixing is provided in the capturing cell 9 for improving binding. In an alternative embodiment the cell culture is provided directly into the magnetic separator instead of into the capturing cell. In this embodiment, the capturing will take place inside the magnetic separator instead of in the capturing cell and the capturing cell is only an intermediate step for storing the magnetic beads.

A3: Providing the cell culture and the magnetic beads from the capturing cell 9 to the magnetic separator 5.

A5: Separating out the magnetic beads with bound biomolecule in the magnetic separator by applying a magnetic force as described above. This step also includes washing out other particles of the feed by using the washing arrangement 13 as described above. Possibly one or more washing cycles are provided where a washing buffer is provided into the magnetic separator when the magnetic beads are bound to parts of magnetic material. The washing buffer is collected outside the magnetic separator and finally a buffer is added to the magnetic separator and the magnetic force is released.

A7: Forwarding the magnetic beads and the buffer in a slurry to the elution cell 7. Before elution the magnetic beads can be packed into a bed as described above—for example by magnetic force, gravitational force, flow packing or by use of an adaptor.

A9: Eluting the bound biomolecule from the magnetic beads by providing an elution buffer from the buffer providing arrangement 8*a* and collecting the eluted biomolecule in the collection arrangement 8*b*. Possibly the elution cell 7 and the magnetic beads are also cleaned in place, CIP, by providing a CIP buffer to the elution cell 7 from the buffer providing arrangement 8*a* and collect the CIP buffer in the collection arrangement 8*b*. And possibly the magnetic beads are also equilibrated by providing an equilibration buffer from the buffer providing arrangement 8*a* and collect the equilibration buffer in the collection arrangement 8*b*. Possibly strip is also performed as described above.

A11: Forwarding the magnetic beads to the capturing cell 9. This step can include pushing out the magnetic beads by forcing an adaptor towards the outlet of the elution cell. It could also include resuspending the bed of magnetic beads in the elution cell by providing an amount of buffer into the elution cell and then the slurry of magnetic beads and buffer could be pumped or pushed out from the elution cell and into the intermediate container 111. Another alternative or complementary can be to remove a retaining arrangement such as a bottom filter or magnetic force keeping the magnetic beads inside the elution cell and pumping or pushing the magnetic beads to the capturing cell 109.

And then the process can continue by adding new cell culture to the capturing cell 9. With this set up it is possible to have two or even three portions of magnetic beads circulating in the system as described above. Hereby one portion is in the magnetic separator 5 while one portion is in the elution cell 7 and one portion can at the same time be in the capturing cell 9 Hereby an effective process for separating a biomolecule is achieved. The system shown in FIG. 1*a* and the process as described in the flow chart in FIG. 3*a* can easily be adapted for the possibility to remove magnetic beads after the elution step and addition of new magnetic beads into the capturing cell 9.

Figure 3B:
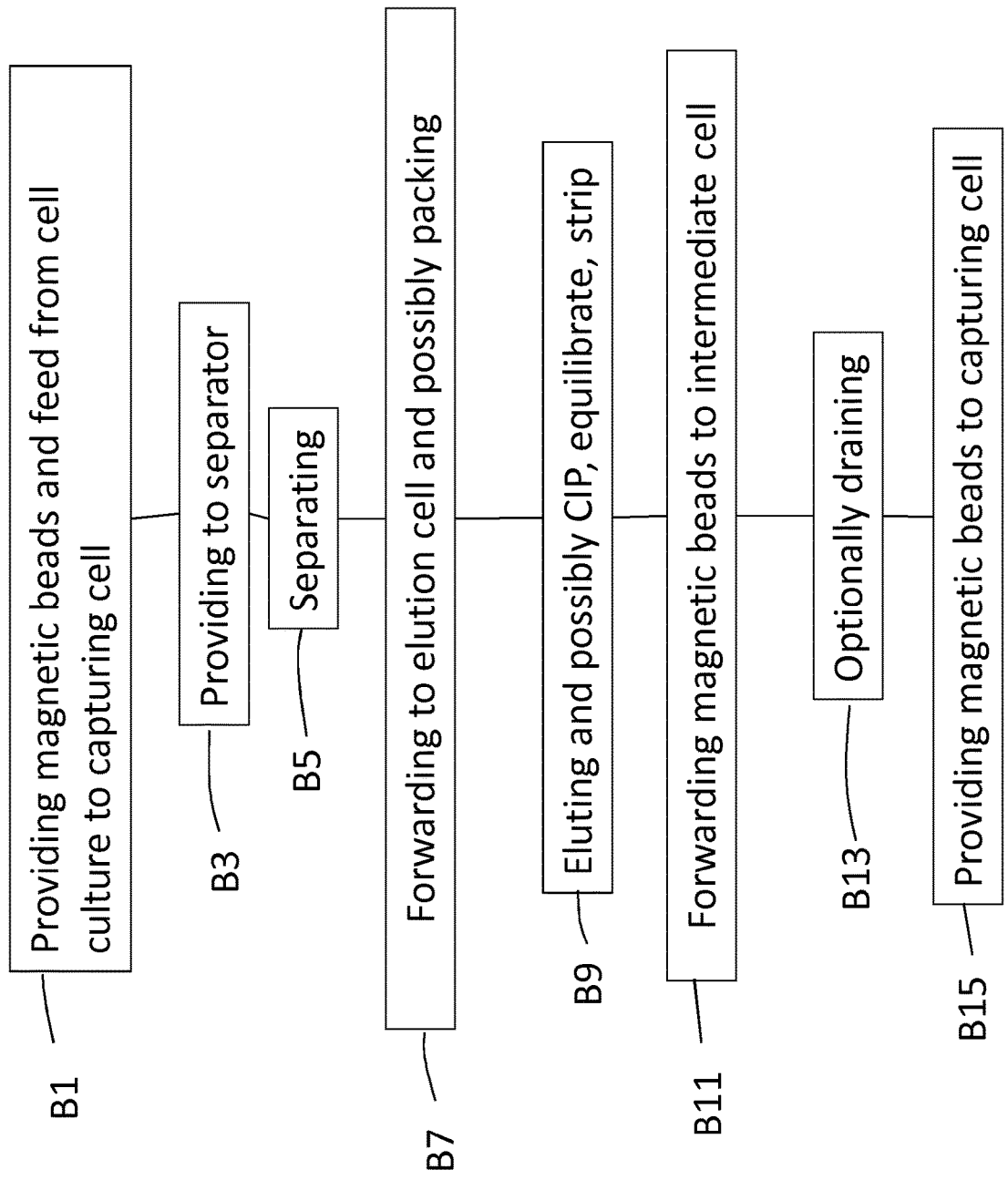
FIG. 3b is a flow chart of a method for separating a biomolecule in the system shown in FIG. 1b.

FIG. 3*b* is a flow chart of a method for separating a biomolecule in the system shown in FIG. 1*b*. The steps of the method are described in order below:

B1: Providing a feed from a cell culture 103 to a capturing cell 109. Said feed comprises a biomolecule to be separated. Also providing to the capturing cell 109 magnetic beads from a magnetic beads storage tank 121 and/or from an intermediate cell 111 provided in the system. If new magnetic beads need to be provided by some reason instead of reusing the magnetic beads from a previous separation these new magnetic beads can be provided from magnetic beads storage tank 121. The magnetic beads comprise ligands capable of binding the biomolecule to be separated. In the capturing cell 109 the biomolecule will bind to the magnetic beads. Possibly mixing is provided in the capturing cell 109 for improving binding.

B3: Providing the cell culture and the magnetic beads from the capturing cell 109 to the magnetic separator 105.

B5: Separating out the magnetic beads with bound biomolecule in the magnetic separator by applying a magnetic force and washing as described above in relation to FIG. 3*a*.

B7: Forwarding the magnetic beads and the buffer in a slurry to the elution cell 107 and possibly packing the magnetic beads as described above.

B9: Eluting the bound biomolecule from the magnetic beads and possibly CIP, equilibrate and strip as described above in relation to FIG. 3*a*.

B11: Forwarding the magnetic beads from the elution cell 107 to an intermediate container 111. This step can include pushing out the magnetic beads by forcing an adaptor towards the outlet of the elution cell. It could also include resuspending the bed of magnetic beads in the elution cell by providing an amount of buffer into the elution cell and then the slurry of magnetic beads and buffer could be pumped or pushed out from the elution cell and into the intermediate container 111. Another alternative or complementary can be to remove a retaining arrangement such as a bottom filter or magnetic force keeping the magnetic beads inside the elution cell and pumping or pushing the magnetic beads to the capturing cell 109.

B13: Optionally draining buffer from the slurry of magnetic beads if buffer was added during the step of forwarding B11 the magnetic beads from the elution cell to the intermediate container. The draining can in one embodiment be provided by providing a magnetic force to the intermediate container 111 which will keep the magnetic beads within the container while buffer can be drained through an outlet 123 to a waste container 125.

B15: Providing the magnetic beads to the capturing cell 109 for reuse in a next separation process. However, in one embodiment parts or all of the magnetic beads could at some stage of the process be taken out from the system to the waste container 125 and be replaced by new magnetic beads provided to the capturing cell 109 from the magnetic beads storage tank 121.

Figure 3C:
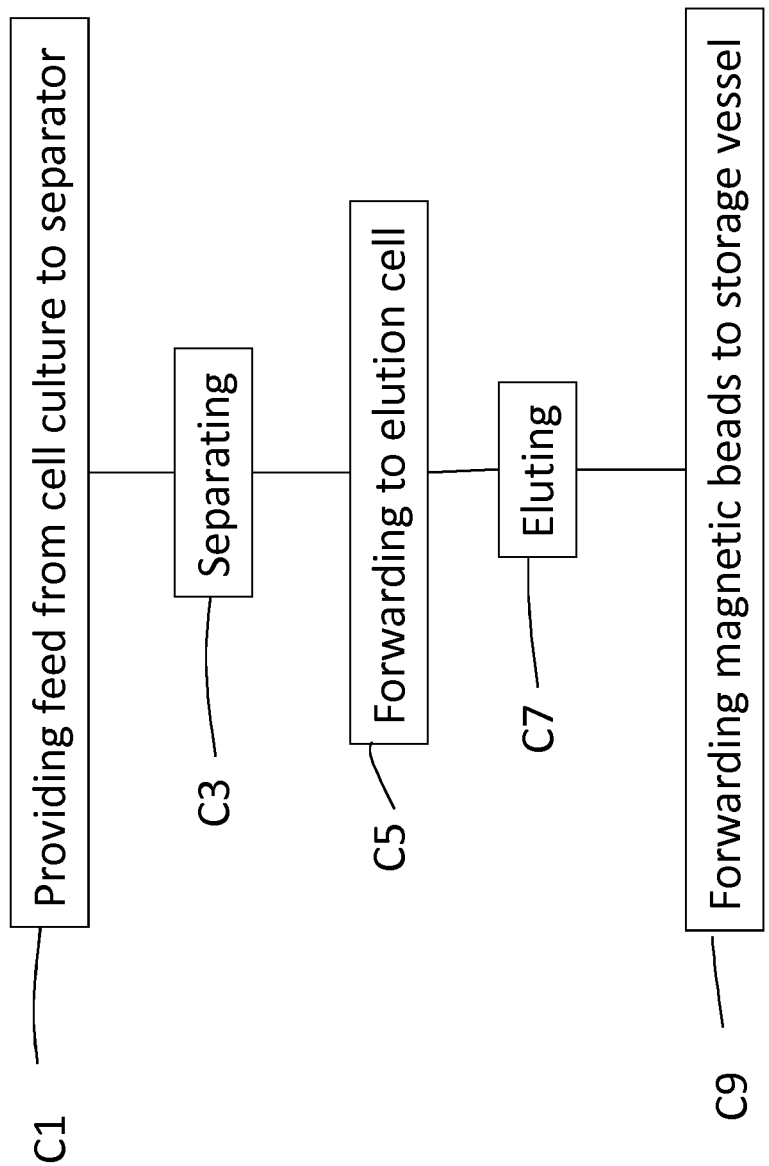
FIG. 3c is a flow chart of a method for separating a biomolecule in the system shown in FIG. 1c.

FIG. 3c is a flow chart of a method for separating a biomolecule in the system shown in FIG. 1c. The steps of the method are described in order below:

C1: Providing a feed directly from a cell culture 203 in to the magnetic separator 205. Magnetic beads have already been provided into the cell culture 203 in this embodiment and the cell culture could thus also be called a capturing cell 209. Said magnetic beads have a ligand binding to the biomolecule to be separated. Alternatively, the magnetic beads could instead be provided directly into the magnetic separator 205 and the biomolecule will bind to the magnetic beads inside the magnetic separator, i.e. cell culture and magnetic beads are provided into the magnetic separator individually.

C3: Separating out the magnetic beads with bound biomolecule in the magnetic separator by applying a magnetic force and washing as described above in relation to FIG. 3a.

C5: Forwarding the magnetic beads and the buffer in a slurry to the elution cell 207 and possibly packing the magnetic beads as described above.

C7: Eluting the bound biomolecule from the magnetic beads and possibly CIP, equilibrate and strip as described above in relation to FIG. 3a.

C9: Forwarding the magnetic beads from the elution cell 207 to a storage vessel 215. This step can include pushing out the magnetic beads by forcing an adaptor towards the outlet of the elution cell. It could also include resuspending the bed of magnetic beads in the elution cell by providing an amount of buffer into the elution cell and then the slurry of magnetic beads and buffer could be pumped or pushed out from the elution cell and into the storage vessel 215. Another alternative or complementary can be to remove a retaining arrangement such as a bottom filter or magnetic force keeping the magnetic beads inside the elution cell and pumping or pushing the magnetic beads to the storage vessel 215.

The method as described in the flow chart of FIG. 3c can be useful when a bioreactor comprising a cell culture should be completely emptied or emptied in a few portions into the magnetic separator for biomolecule separation. It could also be useful when reuse of the magnetic beads by different reason is not suitable.

Figure 4:
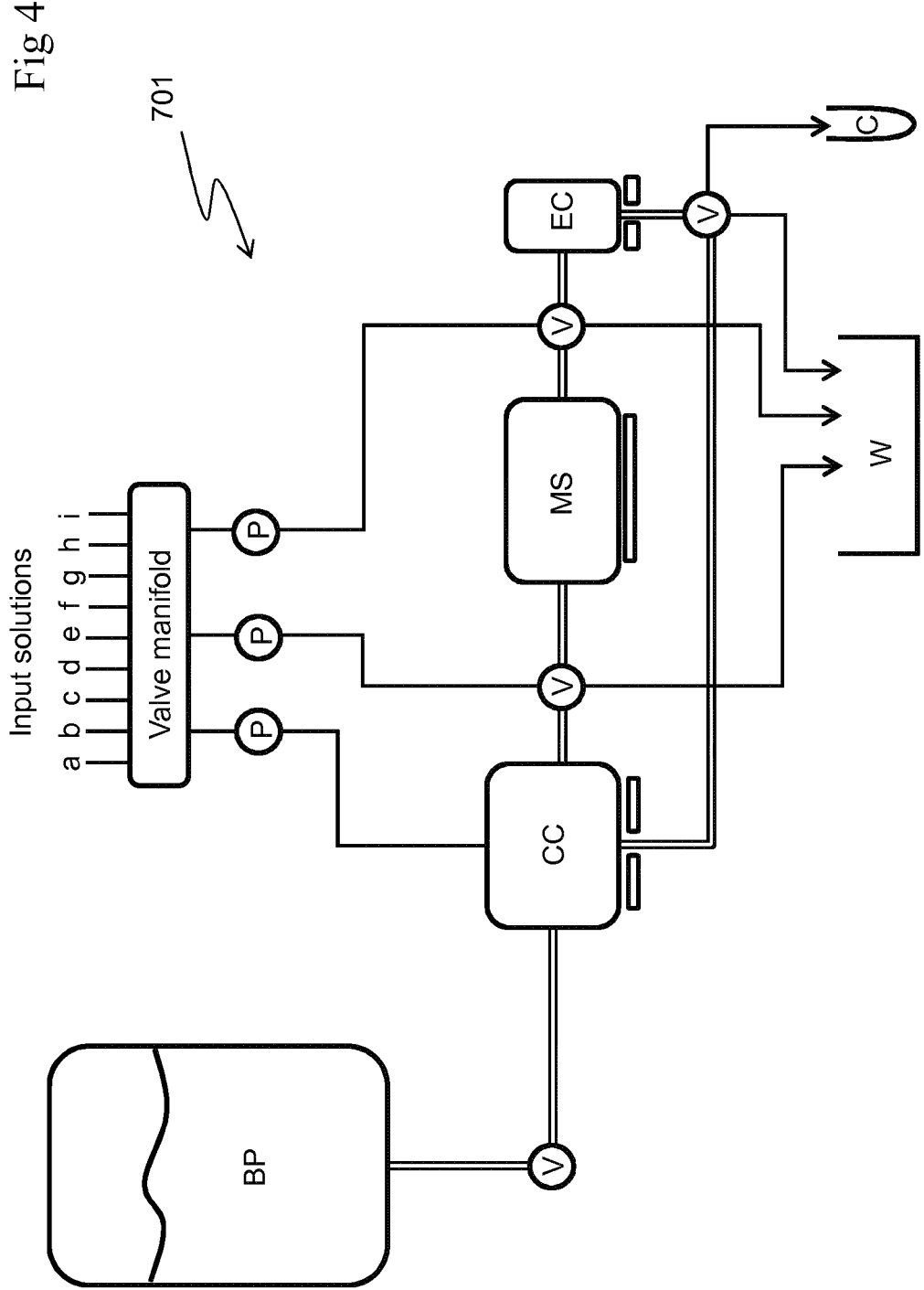
FIGS. 4, 4a-4i show schematically a separation system according to one embodiment of the invention.

FIG. 4 shows a separation system 701 according to one embodiment of the invention. FIGS. 4a-4i show different states of the separation process when using the separation system of FIG. 4. In this embodiment of the invention no pump is needed for moving the magnetic beads in the system. Pumps are used for providing buffer for washing, elution etc. and these buffer flows will push cells and magnetic beads through the system. Hereby a risk for damaging the magnetic beads by pumps is decreased. More detailed description is given below.

Figure 5:
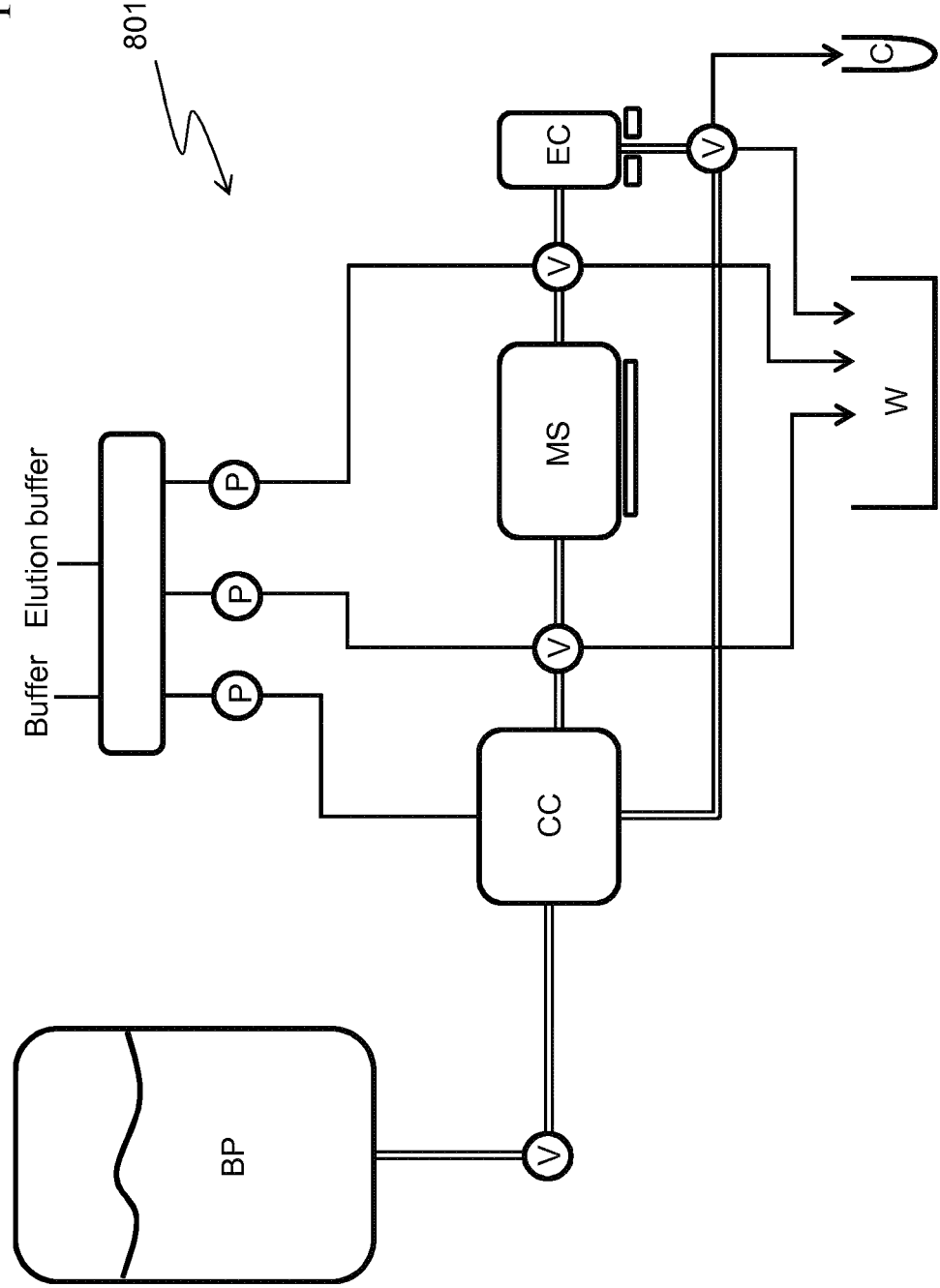

FIG. 5 shows a separation system 801 according to one embodiment of the invention. FIGS. 5a-5f show different states of the separation process when using the separation system of FIG. 5. Also in this embodiment pumps are avoided for moving the magnetic beads. More detailed description is given below.

In FIGS. 4 and 5 EC is elution cell, CC is capturing cell, BP is bioprocess reactor and MS is magnetic separator. P is pumps, V is valves and both pumps and valves may be of suitable type, in one embodiment disposable. A waste container, W, is shown for collecting waste from the different process steps and a vial, C is provided for sample collection.

Fluid flow paths for sample liquid with or without magnetic beads are shown by double lines Fluid flow paths for introduction of fluids and for removal of liquids from the circuit are shown by single lines.

Figure 4A:
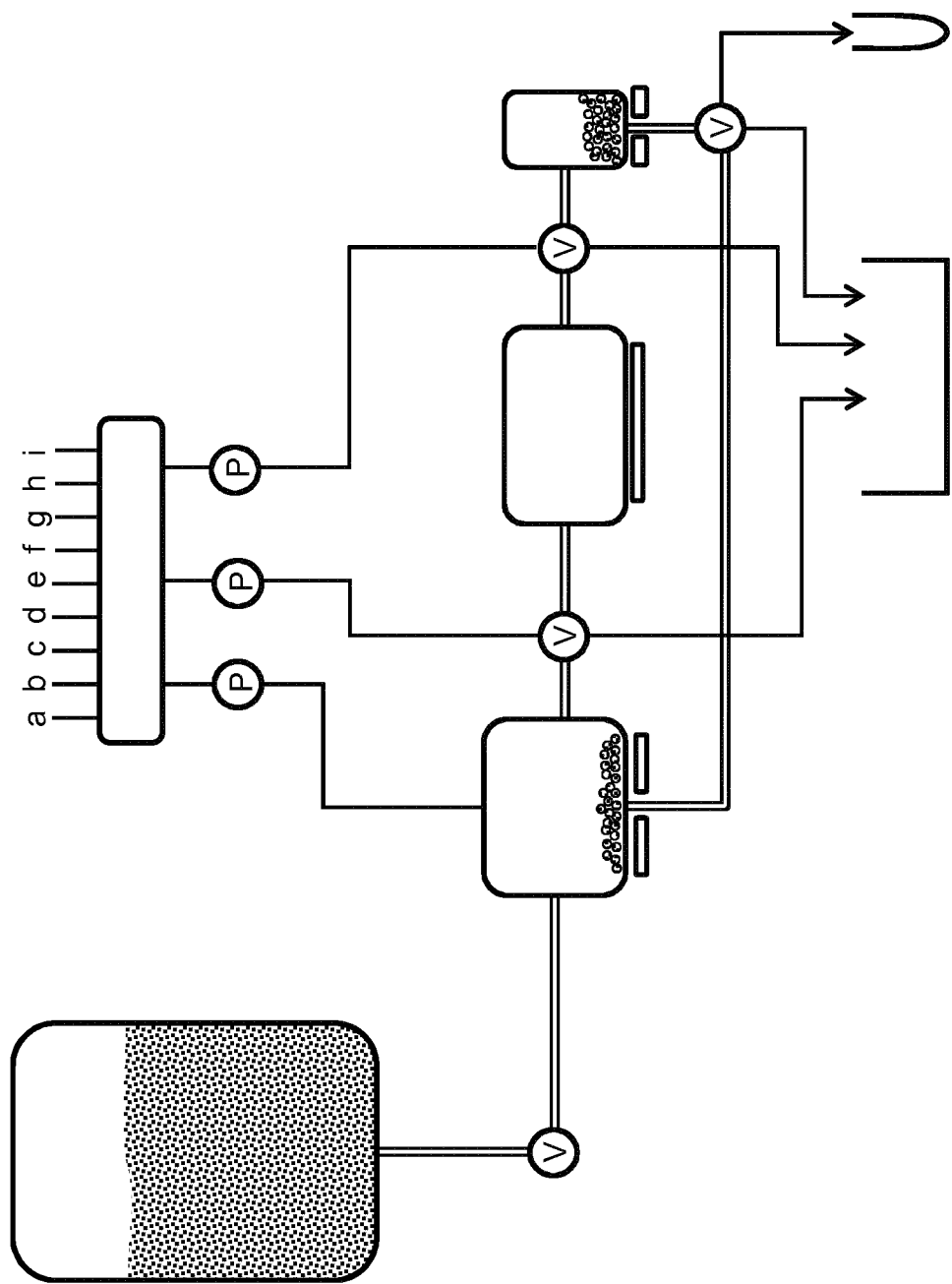

In the system shown in FIG. 4 the capturing cell, CC, the magnetic separator, MS and the elution cell, EC, are provided with magnets for retaining magnetic beads. White magnets means not active, black magnets means activated. The different steps for the process of separation using the system shown in FIG. 4 are shown in FIGS. 4a-4i and are described in order below:

FIG. 4a: Batch mode separation. Initial state comprising two lots of magnetic beads, one in the capturing cell, CC and one in the elution cell, EC. In this state there is no flow in the system.

Figure 4B:
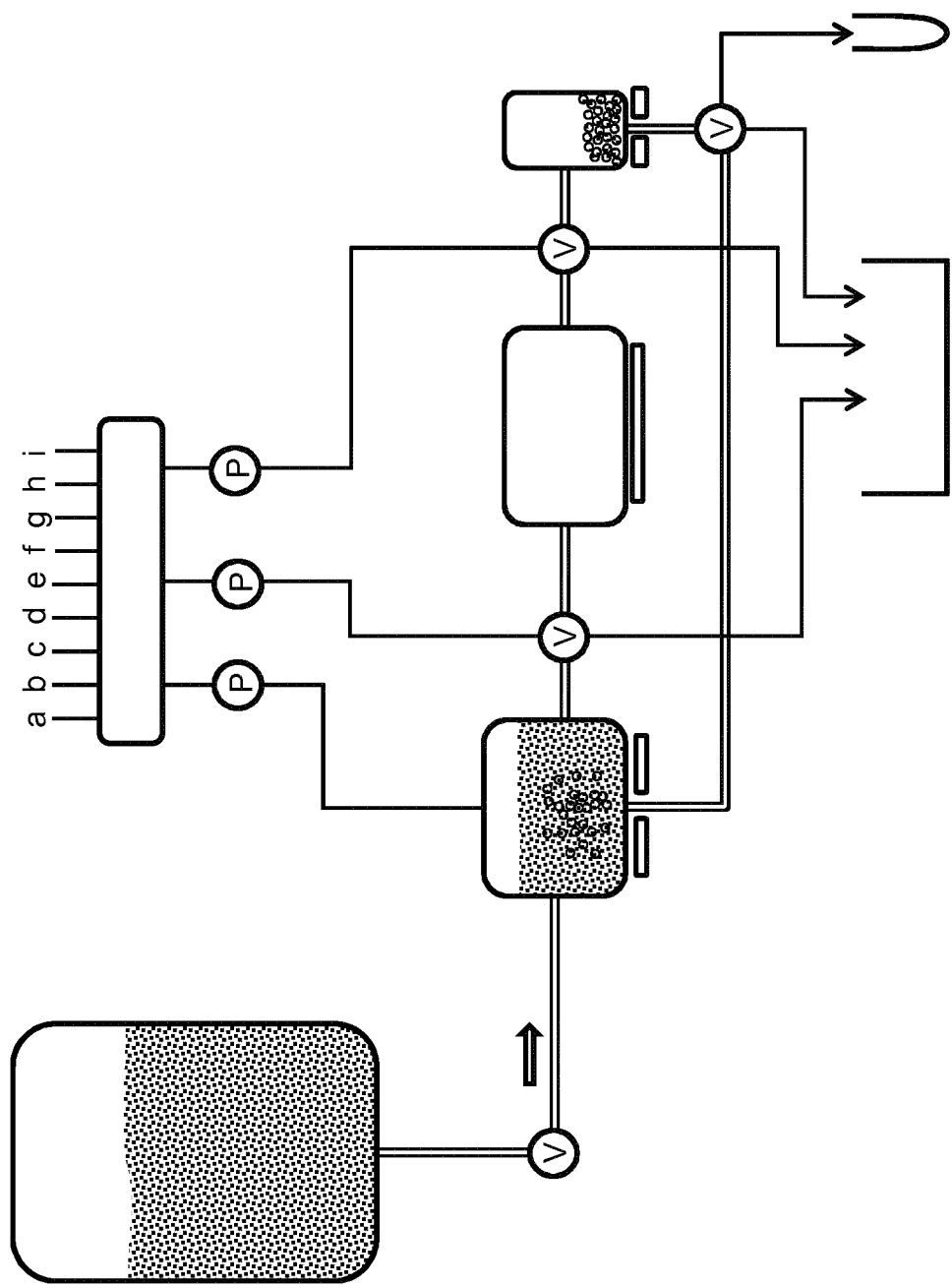

FIG. 4b: Cell culture (feed) is introduced into the capturing cell, CC, from the bioprocess reactor, BP, either by gravity or by a pump (not shown) or by other suitable means. The capturing cell, CC, is preferably agitated in a suitable way, for example by a stirrer, by a wave motion etc. Biomolecules are captured on beads during a predetermined time.

Figure 4C:
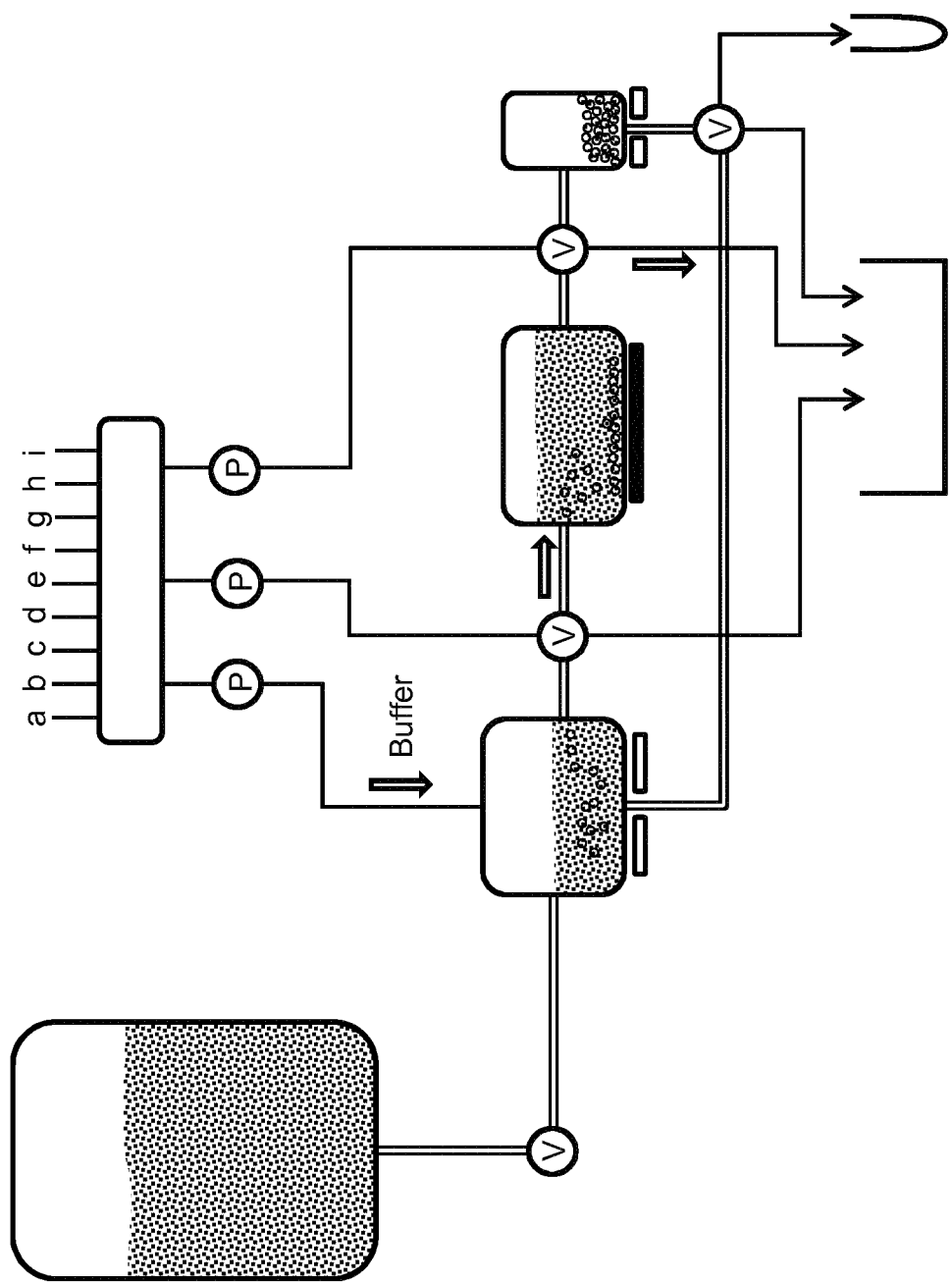

FIG. 4c: Buffer is pumped into the capturing cell, CC, to push the feed and magnetic beads into the magnetic separator, MS. The magnet in the magnetic separator, MS, is activated to capture the magnetic beads and the rest of the feed is passed on to waste, W.

Figure 4D:
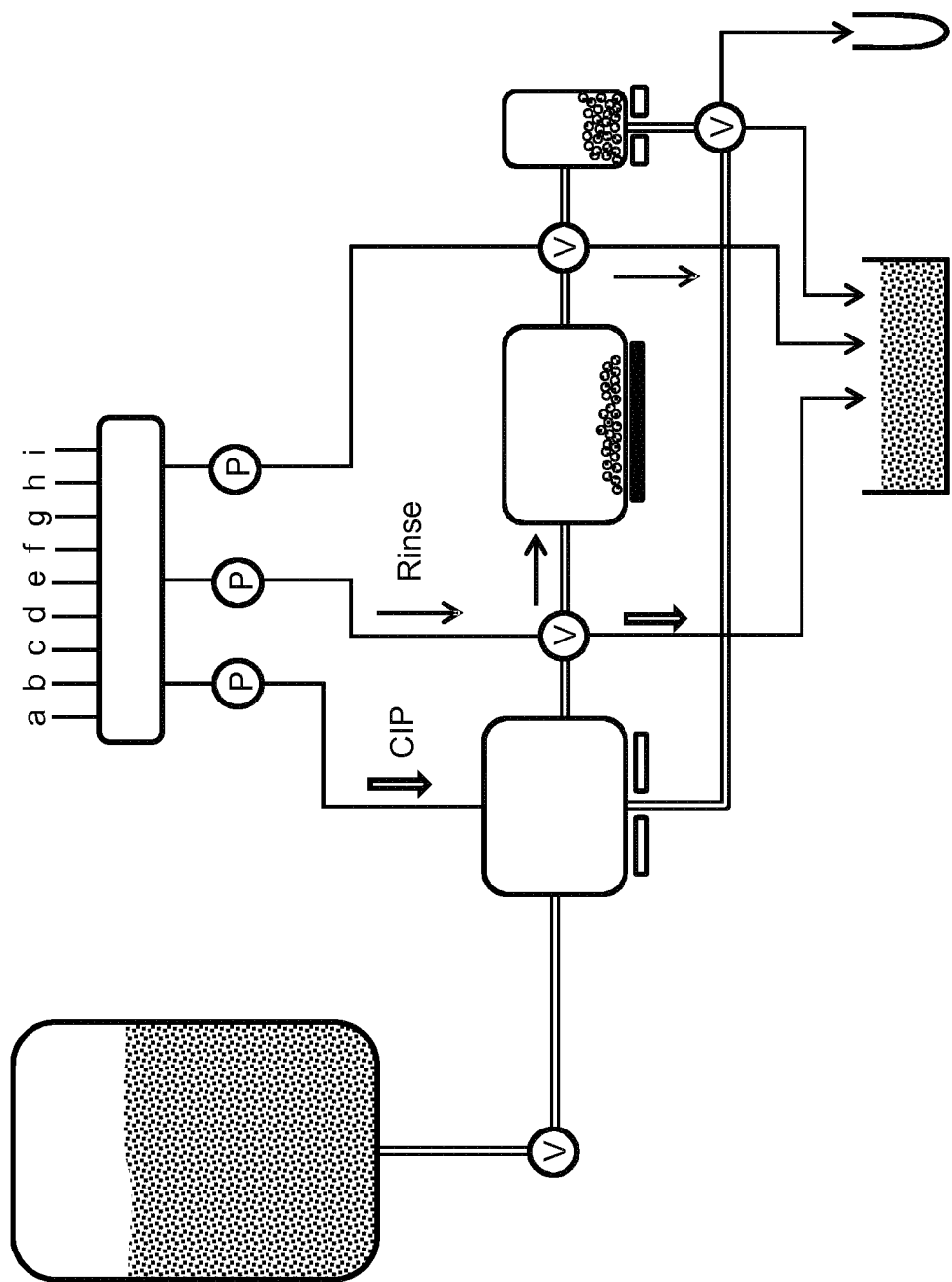

FIG. 4d: CIP solution(s) are pumped into the capturing cell, CC, and drained through a valve to waste, W (may involve several steps). Rinse solution(s) is/are pumped through the magnetic separator, MS, to remove cells etc. and forwarded to waste, W. This may be performed several times and the magnet may be deactivated to suspend the magnetic beads and then reactivated to capture the magnetic beads again during rinse.

Figure 4E:
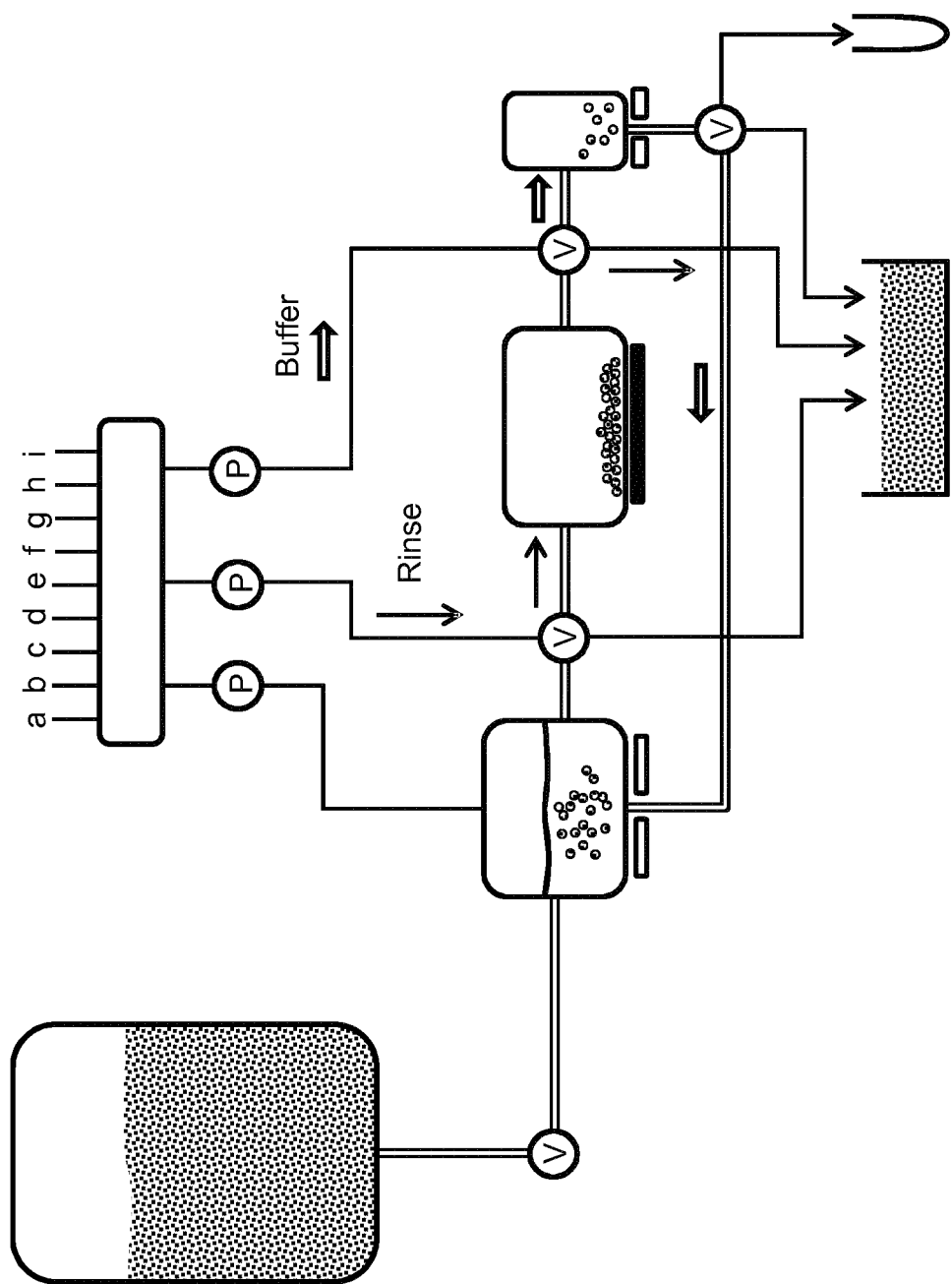

FIG. 4e: Once the capturing cell, CC, is clean magnetic beads are pushed from the elution cell, EC, to the capturing cell, CC, by pumping buffer. Rinse of the magnetic separator, MS, continues (optional).

Figure 4F:
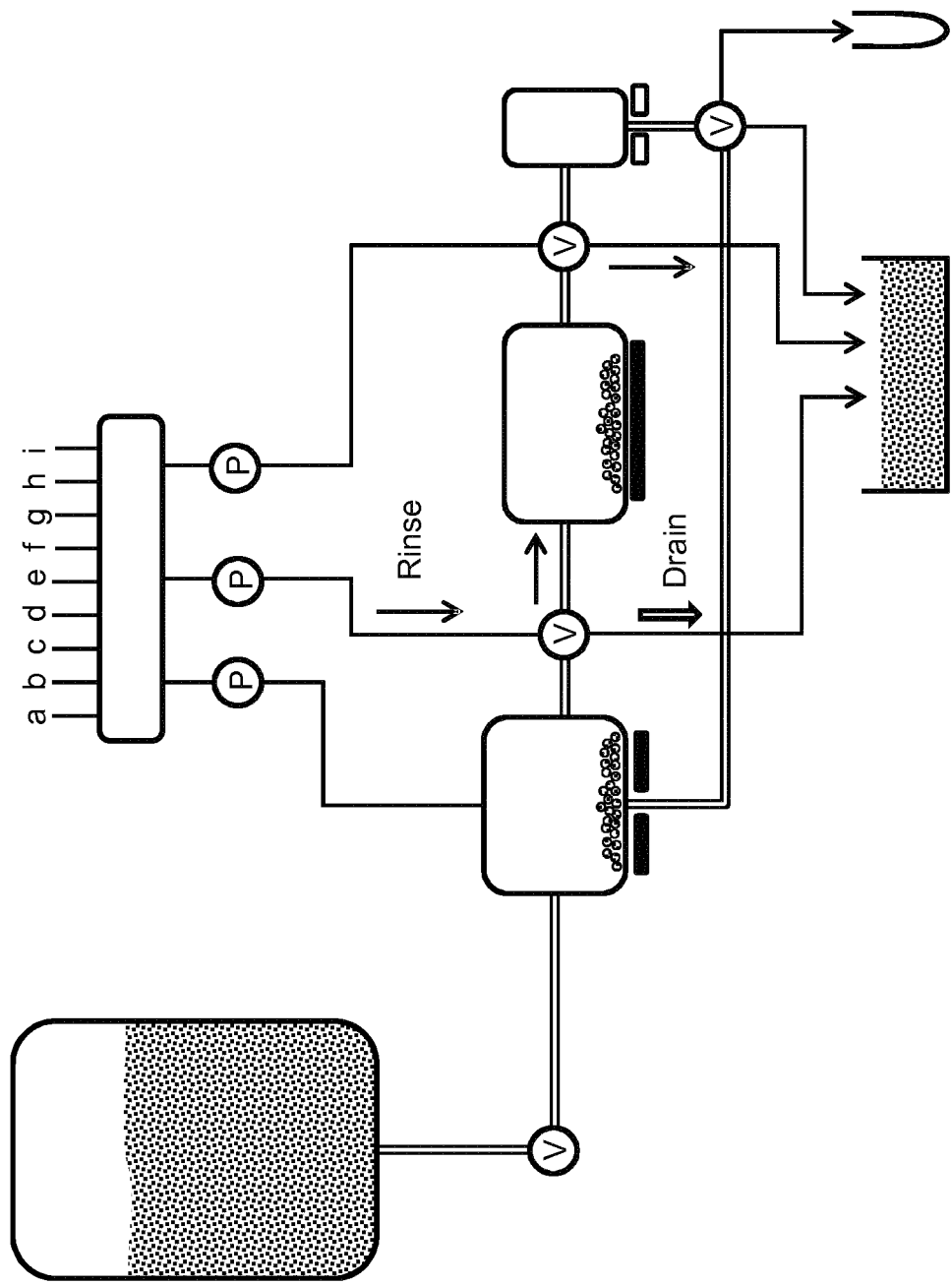

FIG. 4f: Excess buffer is removed from the capturing cell, CC, by draining through a valve. In this embodiment this is performed passively, i.e. by gravity. This step is optional depending on if it is acceptable to dilute the feed or not. Rinse is continued (if necessary)—alternatively the beads may be pushed/flushed from the magnetic separator, MS, to the elution cell, EC, see 4g.

Figure 4G:
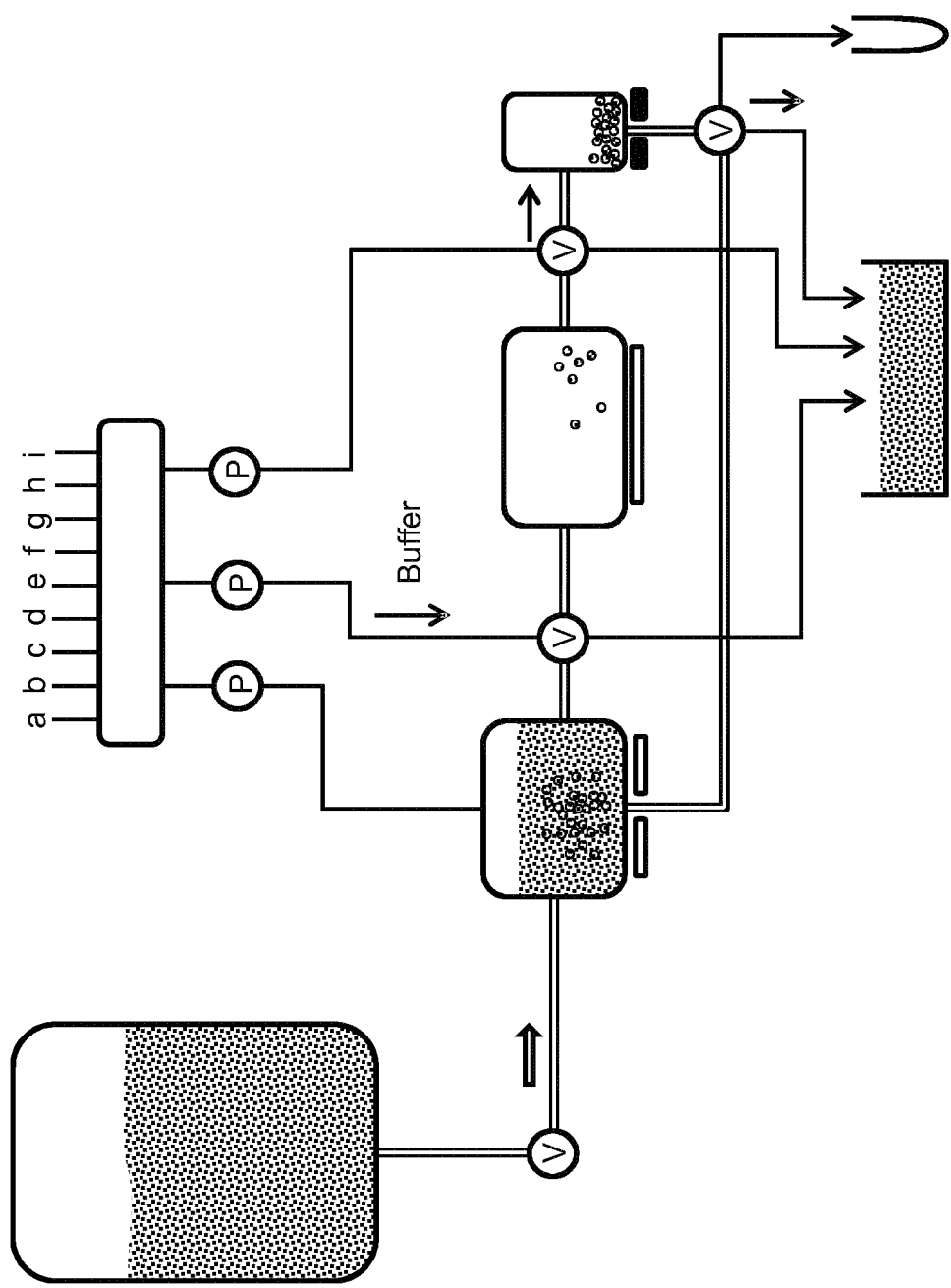

FIG. 4g: Feed is added to the capturing cell, CC, from the bioprocess reactor, BP. Magnetic beads may be pushed/flushed from the magnetic separator, MS, to the elution cell, EC, and captured therein by an activated magnet at the outlet.

Figure 4H:
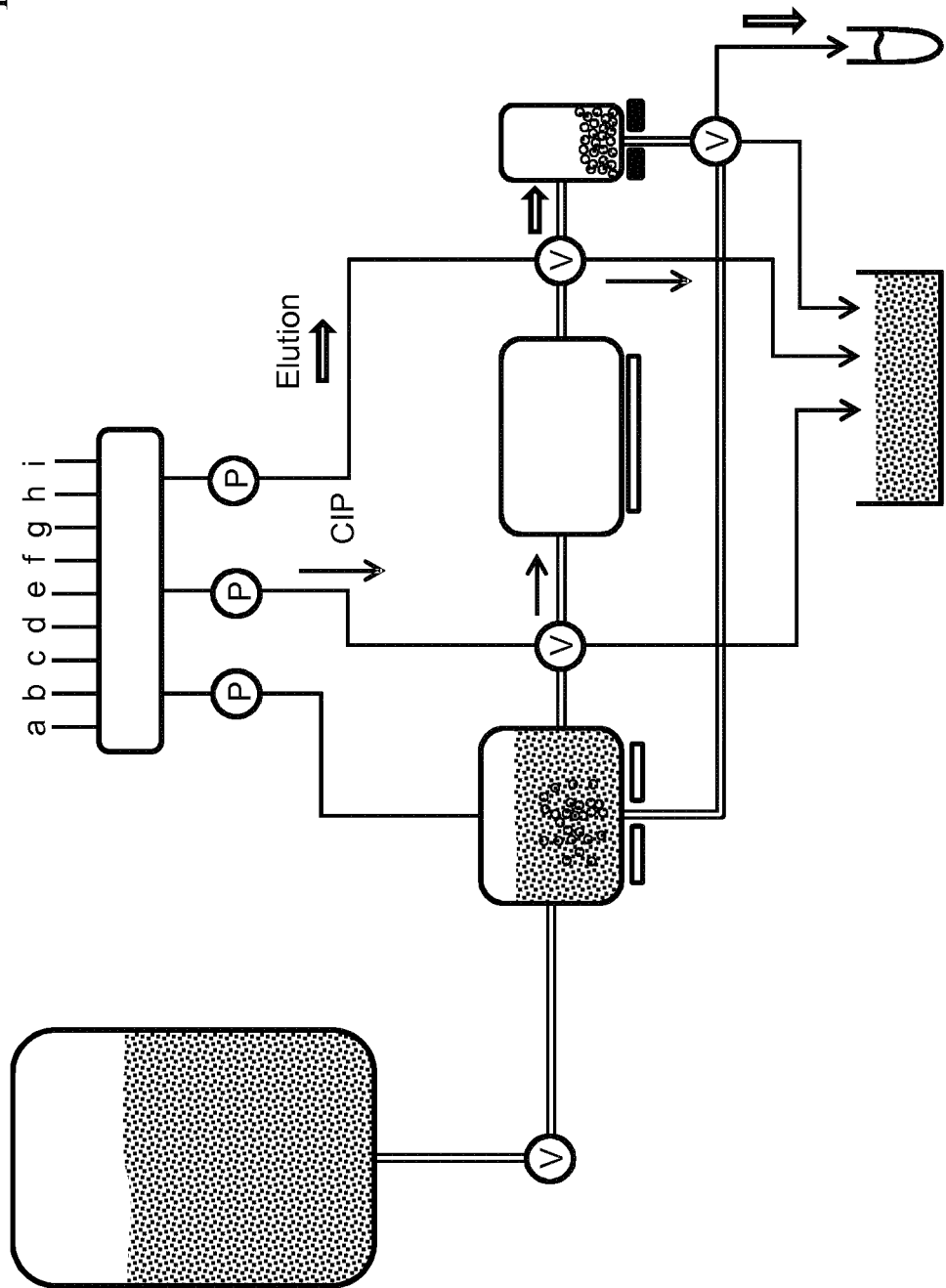

FIG. 4h: Biomolecules are captured on beads during a predetermined time in the capturing cell, CC. Biomolecules are eluted from beads in the elution cell, EC. Eluted product is collected in the vial, C.

Figure 4I:
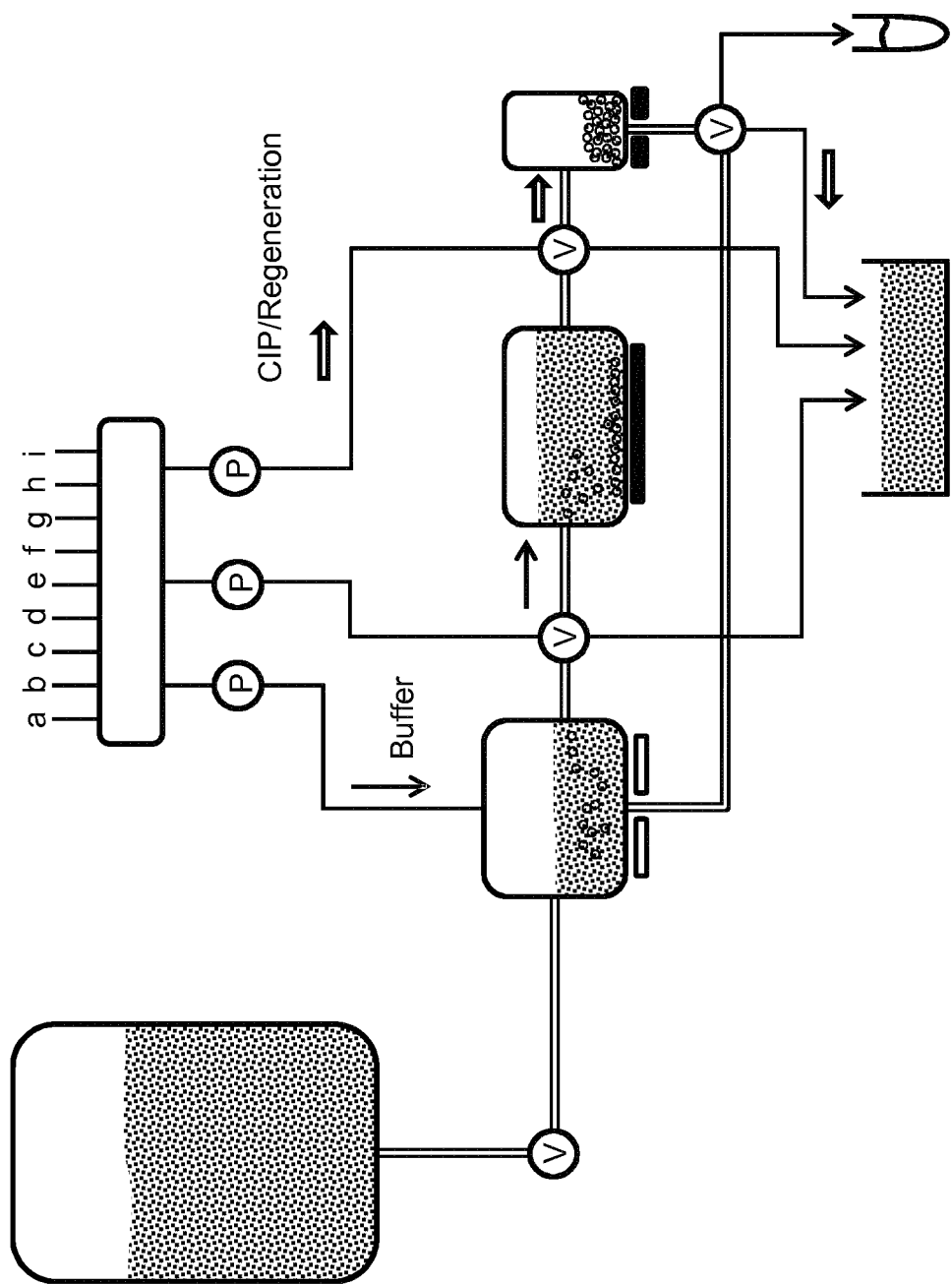

FIG. 4i: Buffer is pumped into the capturing cell, CC, to push feed and magnetic beads into the magnetic separator, MS. The magnet in the magnetic separator, MS, is activated to capture the magnetic beads and the feed is passed on to waste, W. The magnetic beads are washed and reactivated in the elution cell, EC.

Then loop 4d-4i until the bioprocess reactor, BP, is empty.

FIG. 5 shows a simplified process without cleaning and wash steps in the capturing cell, CC, and the elution cell, EC. The process steps of the separation process performed in the system shown in FIG. 5 are described below with reference to FIGS. 5a-5f.

Figure 5A:
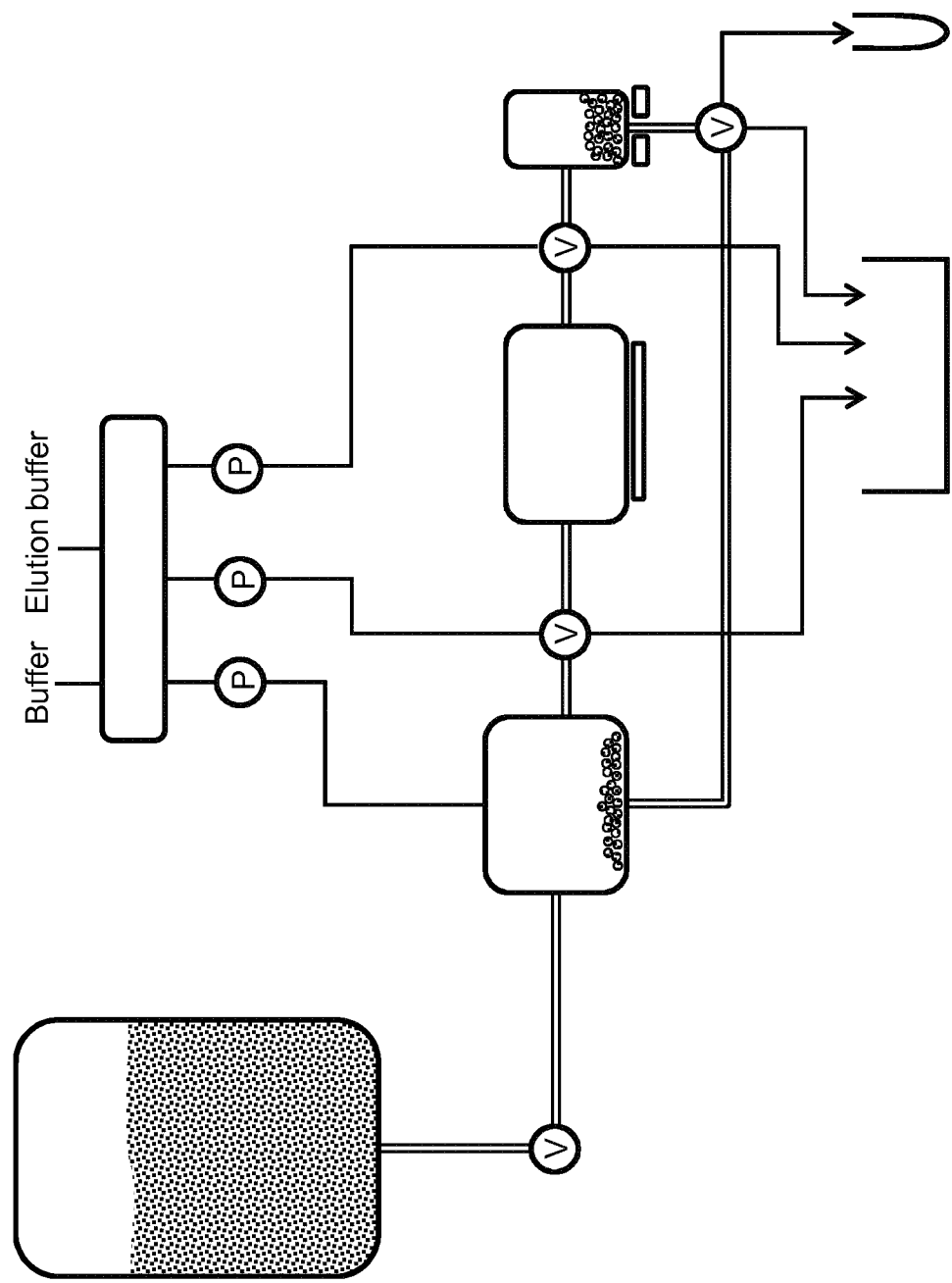

FIG. 5a: initial state comprising two lots of magnetic beads, one in the capturing cell, CC and one in the elution cell, EC. In this state there is no flow in the system.

Figure 5B:
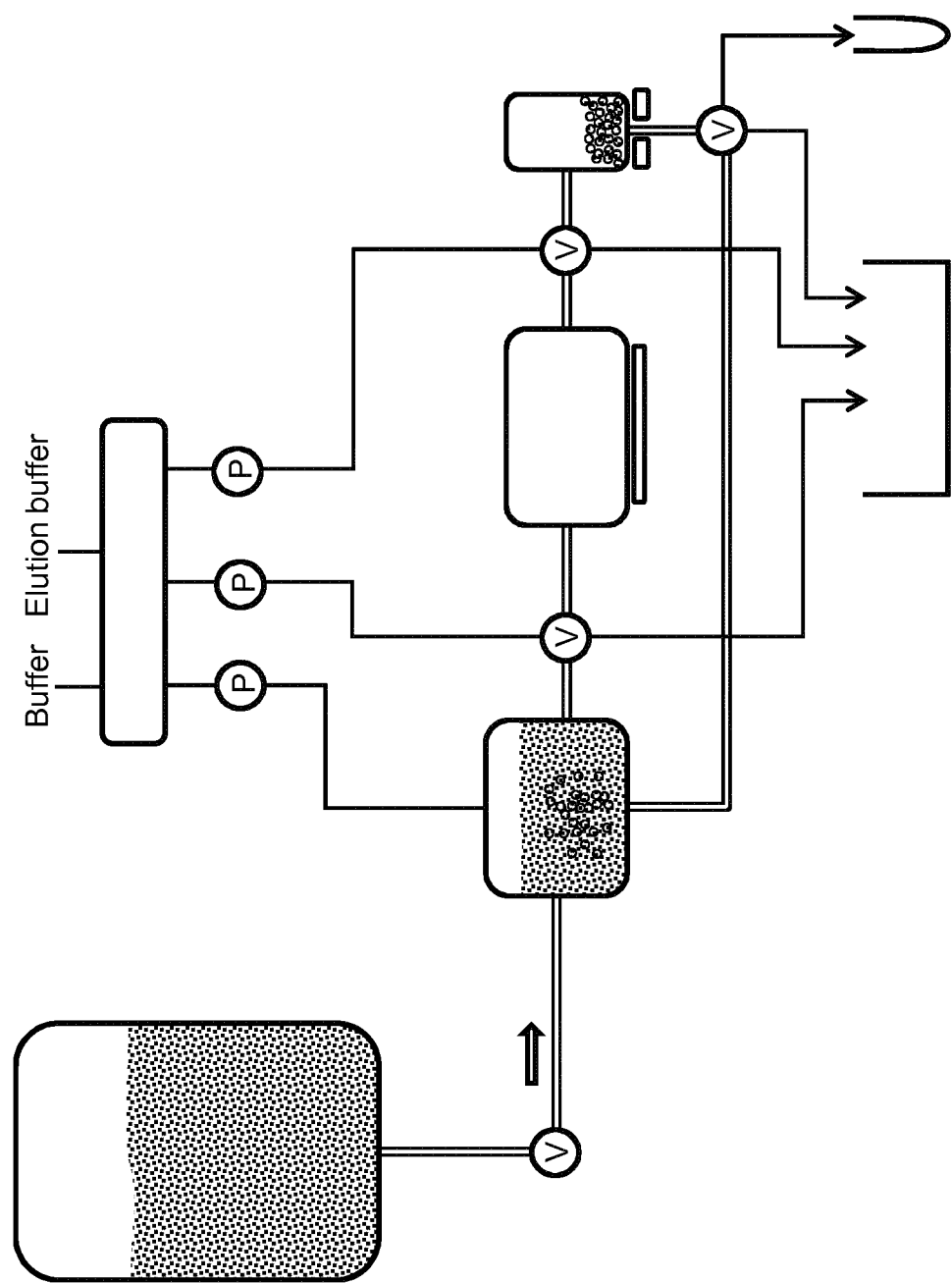

FIG. 5b: Feed is added to the capturing cell, CC, from the bioprocess reactor, BP.

Figure 5C:
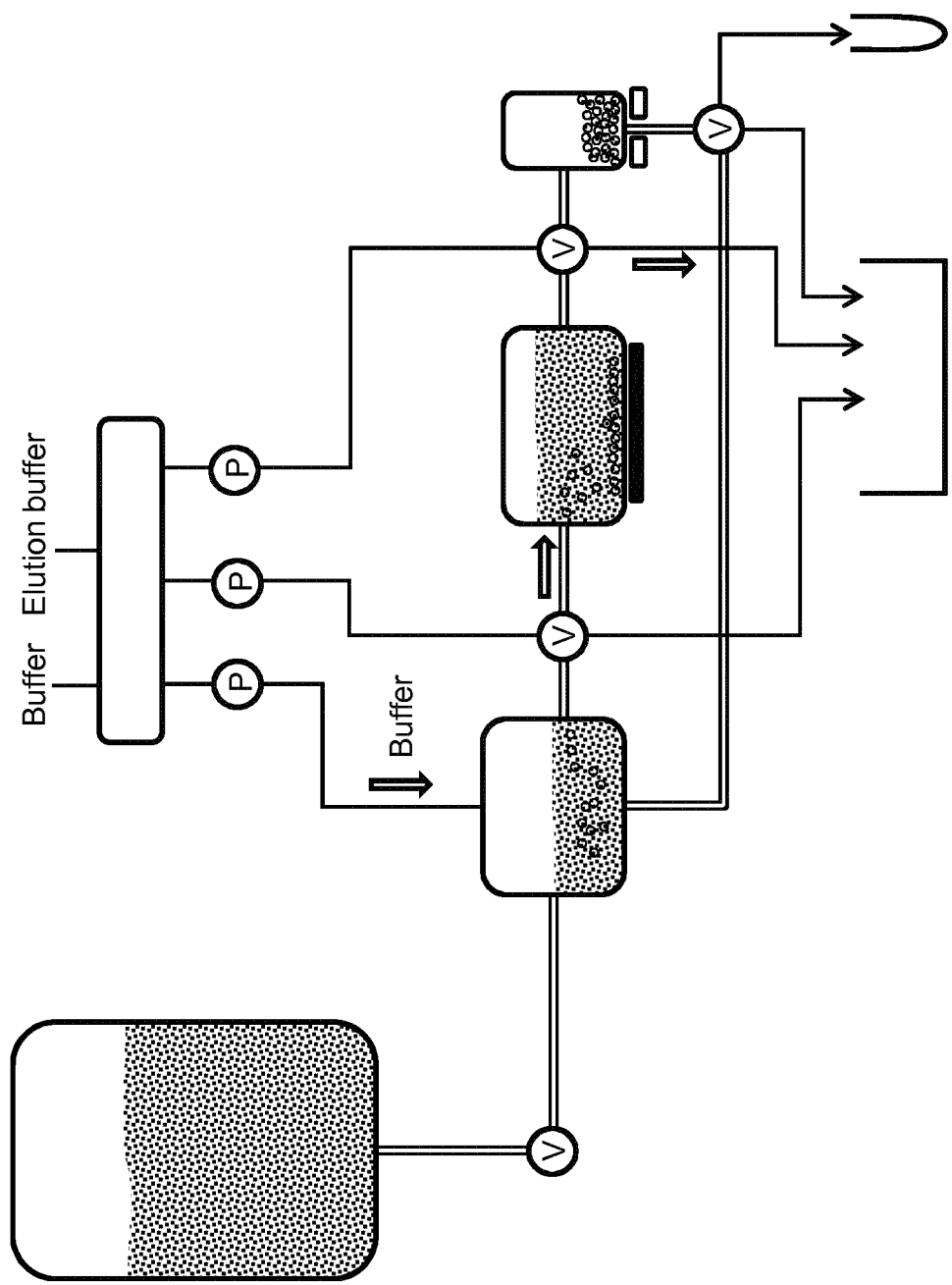

FIG. 5c: Buffer is pumped into the capturing cell, CC, to push feed and magnetic beads into the magnetic separator, MS. The magnet in the magnetic separator, MS, is activated to capture the magnetic beads and the feed is passed on to waste, W.

Figure 5D:
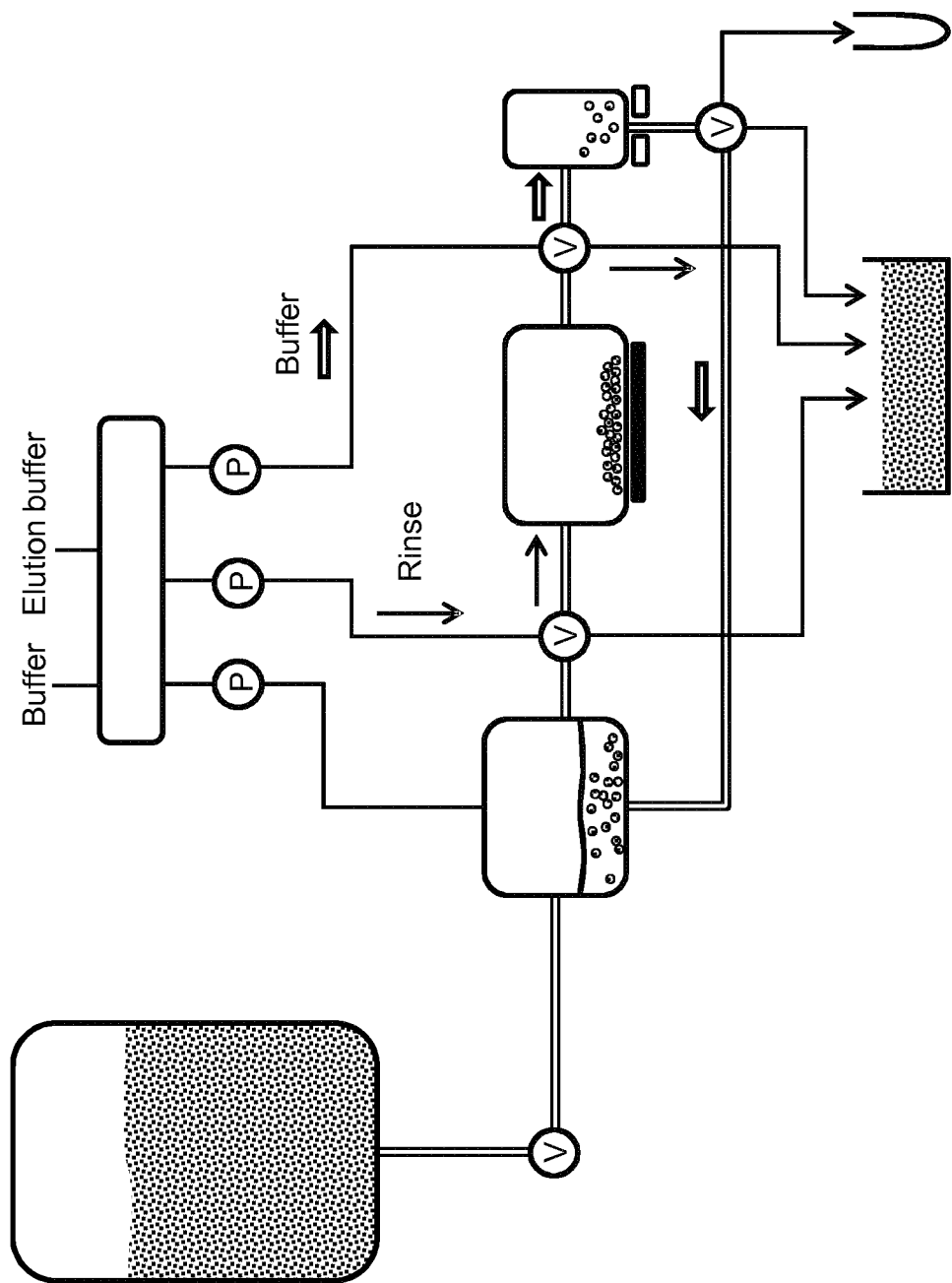

FIG. 5d: Rinse solution(s) is pumped through the magnetic separator, MS, to remove cells etc. The magnetic beads are pushed from the elution cell, EC, to the capturing cell, CC, by pumping buffer.

Figure 5E:
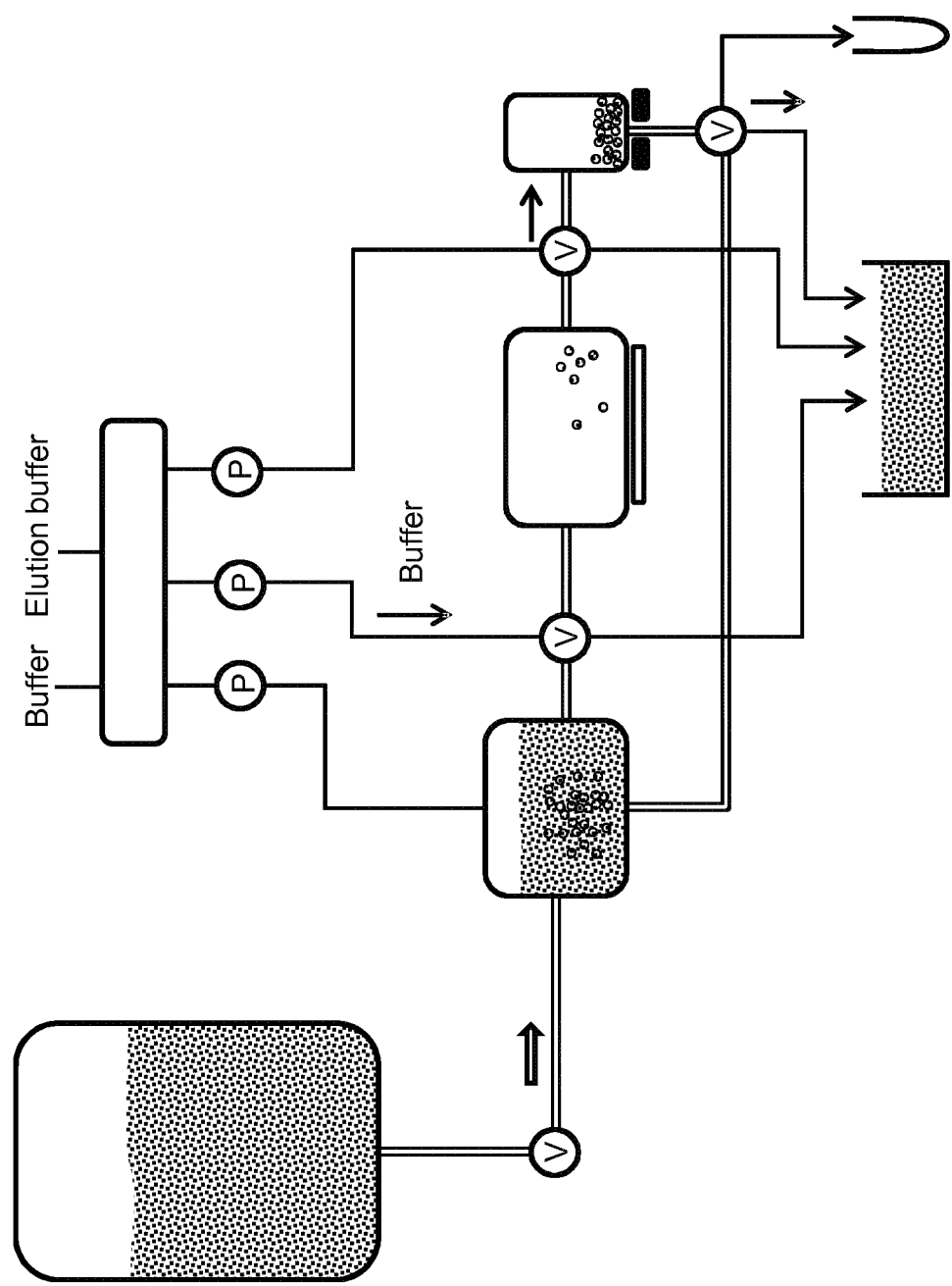

FIG. 5e: Feed is added to the capturing cell, CC, from the bioprocess reactor, BP. Magnetic beads are pushed/flushed from the magnetic separator, MS, to the elution cell, EC, and captured therein by an activated magnet at the outlet.

FIG. 5f: Biomolecules are captured on the magnetic beads during a predetermined time in the capturing cell, CC. Biomolecules are eluted from the magnetic beads in the elution cell, EC, and eluted product is collected in the vial, C.

Then repeat 5d, 5e, 5f until batch is completed.

To achieve highest possible concentration, elution is performed in batch mode by contacting the beads with a predetermined volume of elution buffer during a predetermined time. The elution buffer including eluted target sample is collected in elution vial. Then the magnetic beads (including remaining target sample) are forwarded to the capture cell without CIP.

In these systems, the magnetic beads (and the cells) do not have to pass through any pump where there is an increased chance that they are damaged. The general process disclosed in the figures may be applied also using pumps in the loop in case it can be verified that beads are not damaged or in case debris from damaged beads is ok in the process. Some steps in the loop may be facilitated by gravity by placing one cell above the subsequent cell. E.g. the elution cell, EC, may be arranged above the capturing cell, CC, in order to facilitate transport of magnetic beads from the elution cell, EC, to the capturing cell, CC, and to reduce the amount of buffer needed for this transport.

The invention claimed is:

1. A method for separating a biomolecule from a cell culture in a separation system, comprising the steps of:
    providing a feed from a cell culture comprising said biomolecule to a magnetic separator and providing to the magnetic separator magnetic beads comprising ligands which bind said biomolecule;
    separating by the magnetic separator said magnetic beads with the bound biomolecule from the rest of the feed;
    forwarding said magnetic beads from the magnetic separator as a slurry with an added buffer to an elution cell, wherein the elution cell comprises an inlet in connection with an outlet from the magnetic separator, and a retaining arrangement for keeping the magnetic beads within the elution cell and allowing excess buffer to escape from the elution cell;
    packing the slurry of said magnetic beads in the elution cell to provide a bed of magnetic beads within the elution cell with a void volume less than 60%; and
    eluting the bound biomolecule in the elution cell.

2. The method according to claim 1, further comprising forwarding the magnetic beads from the elution cell for reuse in the magnetic separator.

3. The method according to claim 1, further comprising a step of:
    mixing the feed from the cell culture and the magnetic beads in a capturing cell before they are provided to the magnetic separator allowing the biomolecule to bind to the magnetic beads.

4. The method according to claim 1, wherein the step of separating comprises:
    applying a magnetic field to the magnetic separator allowing the magnetic beads to bind magnetically to parts of magnetic material inside the magnetic separator;
    washing out other components from the magnetic separator than those magnetically bound to the parts of magnetic material; and
    wherein the step of forwarding said magnetic beads to an elution cell comprises releasing the magnetic field to the magnetic separator before the magnetic beads are forwarded.

5. The method according to claim 1, wherein the method further comprises the steps of:
    cleaning in place, (CIP), of the elution cell and the magnetic beads after the elution; and
    contacting the magnetic beads with an equilibration buffer in the elution cell after the CIP and before the forwarding of the magnetic beads from the elution cell.

6. The method according to claim 1, wherein a new portion of feed from the cell culture and magnetic beads are provided into the magnetic separator while a previous portion is in the elution cell, whereby at least two portions of magnetic beads are circulating in the separation system.

7. The method according to claim 6, wherein a new portion of feed from the cell culture and magnetic beads are provided into the magnetic separator while one previous portion is in the elution cell and one previous portion is in a capturing cell, whereby three portions of magnetic beads are circulating in the separation system.

8. The method according to claim 1, further comprising a first step of connecting the parts of the separation system by pre-sterilized, flexible tubing and aseptic connectors.

9. The method according to claim 1, wherein the step of packing further comprises pushing an adaptor inside the elution cell while keeping the magnetic beads inside the elution cell by the retaining arrangement and allowing buffer to escape from the elution cell.

10. The method according to claim 1, wherein the step of packing further comprises allowing the magnetic beads to build a packed bed in a lower part of the elution cell by gravity force and/or a magnetic force while allowing excess buffer to escape from the elution cell.

11. The method according to claim 1, wherein the step of packing further comprises flow packing the magnetic beads by flowing the slurry of magnetic beads into the inlet of the elution cell, which elution cell comprises an adaptor positioned at a start position in the elution cell when a slurry of magnetic beads starts to fill the elution cell, said start position being closer to the inlet of the elution cell than an end position of the adaptor, said end position corresponding to the position of the adaptor when the filling of magnetic beads into the elution cell is completed, said adaptor keeping a force towards the flow direction of the slurry and allowing buffer to escape though the adaptor during packing.

12. The method according to claim 1, further comprising a step of releasing the retaining arrangement in the elution cell after elution and forwarding the magnetic beads from the elution cell for reuse in the magnetic separator.

13. The method according to claim 12, wherein releasing the retaining arrangement further comprises opening a bottom closure, removing a bottom filter or removing a magnetic force.

14. The method according to claim 12, wherein the forwarding of the magnetic beads is performed by pushing an adaptor in the elution cell towards the outlet of the elution cell.

15. The method according to claim 12, wherein the step of forwarding the magnetic beads from the elution cell for reuse in the magnetic separator further comprises a step of adding a buffer to the elution cell for re-suspending the bed and pumping or pushing out the magnetic beads from the elution cell.

16. The method according to claim 12, wherein the step of forwarding the magnetic beads from the elution cell for reuse in the magnetic separator further comprises a step of forwarding the magnetic beads from the elution cell to an intermediate cell wherein excess buffer can be removed.

17. The method according to claim 16, wherein excess buffer is removed from the intermediate cell by keeping the magnetic beads inside the intermediate cell by magnetic force while draining the intermediate cell from buffer.

18. The method of claim 1, wherein the retaining arrangement is non-magnetic.

* * * * *